United States Patent
Chang et al.

(10) Patent No.: US 9,546,354 B2
(45) Date of Patent: Jan. 17, 2017

(54) Z CELLS ACTIVATED BY ZINC FINGER-LIKE PROTEIN AND USES THEREOF IN CANCER TREATMENT

(71) Applicant: National Cheng Kung University, Tainan (TW)

(72) Inventors: Nan-Shan Chang, Owega, NY (US); Chen-Yu Lu, Taipei (TW); Wan-Pei Su, Nantou (TW); Yu-An Chen, Taipei (TW); Wang Wan Jen, New Taipei (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 14/281,194

(22) Filed: May 19, 2014

(65) Prior Publication Data

US 2015/0329824 A1    Nov. 19, 2015

(51) Int. Cl.
*A61K 38/00*    (2006.01)
*C12N 5/078*    (2010.01)
*A61K 39/00*    (2006.01)

(52) U.S. Cl.
CPC ......... *C12N 5/0648* (2013.01); *A61K 39/0011* (2013.01); *A61K 2039/515* (2013.01); *C12N 2501/48* (2013.01); *C12N 2501/998* (2013.01)

(58) Field of Classification Search
CPC .............................. C12N 5/0648; A61K 38/00
USPC .......................................................... 435/325
See application file for complete search history.

(56) References Cited

U.S. PATENT DOCUMENTS

| | | |
|---|---|---|
| 6,130,087 A | 10/2000 | Srivastava et al. |
| 2012/0238020 A1* | 9/2012 | Mitchell ................ C12M 23/58 |
| | | 435/377 |
| 2014/0135272 A1 | 5/2014 | Chang et al. |

FOREIGN PATENT DOCUMENTS

WO    WO 2013/009948 A2    1/2013

OTHER PUBLICATIONS

Hong et al., Zfra affects TNF-mediated cell death by interacting with death domain protein TRADD and negatively regulates the activation of NF-kappaB, JNK1, p53 and WOX1 during stress response. BMC Mol Biol. Jun. 13, 2007;8:50.
Su et al., Self-polymerizing Zfra peptides elicit immune response for targeting cancer. The FASEB Journal. Apr. 23, 2012;26(1):967.6.
Chang, Abstract 4621: Zfra regulates protein degradation and provides strong prevention against skin cancer. Cancer Res. Apr. 15, 2011;71(8 Supplement):4621. doi: 10.1158/1538-7445.AM2011-4621.

* cited by examiner

*Primary Examiner* — Yan Xiao
(74) *Attorney, Agent, or Firm* — Wolf, Greenfield & Sacks, P.C.

(57) ABSTRACT

Immune cells (Z cells) activated by zinc finger-like protein that regulates apoptosis (Zfra) and uses thereof in cancer treatment.

5 Claims, 26 Drawing Sheets

B80: Cl-4AS-1

B81: Cl-4AS-1 + Zfra (4-10)

B82: (±)-Blebbistatin

B83: (±)-Blebbistatin + Zfra (4-10)

S133 PBS

S134 B78 spleen cells transfer

S136 B80 spleen cells transfer

S135 B79 spleen cells transfer

S137 B81 spleen cells transfer

S138 B82 spleen cells transfer

S149: DMSO + PBS

S150: Zfra (4-10)

S152: Cl-4AS-1 + Zfra (4-10)

S153: (±)-Blebbistatin

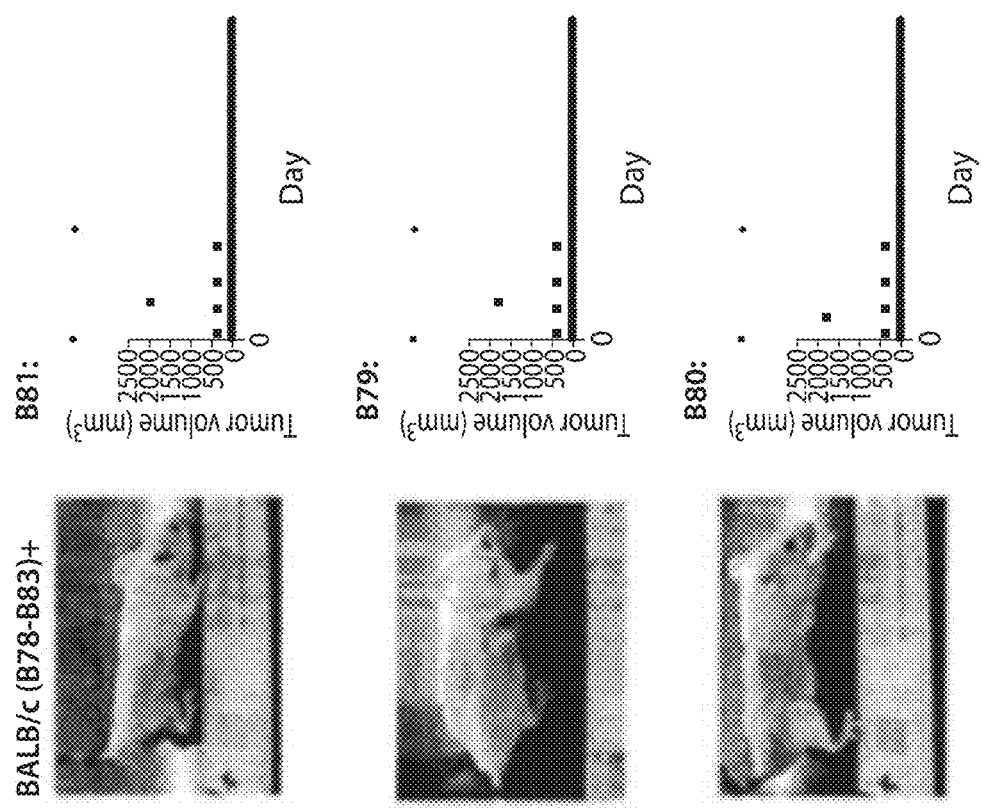

Z CELLS ACTIVATED BY ZINC FINGER-LIKE PROTEIN AND USES THEREOF IN CANCER TREATMENT

BACKGROUND OF THE INVENTION

Zinc finger-like protein that regulates apoptosis (Zfra) is a naturally-occurring small peptide consisting of 31 amino acid residues. Zfra regulates tumor necrosis factor (TNF)-mediated cell death by binding to and inhibiting proteins involved in the TNF signaling pathway, including tumor suppressor WWOX (through the first WW domain and ADH/SDR domain), TNF receptor- or Fas-associated death domain proteins (TRADD and FADD), and receptor-interacting protein (RIP). Hong, et al., 2007, *BMC Mol Biol*, 8, 50. Moreover, Zfra sequesters cJun N-terminal kinase 1 (JNK1), p53, WWOX, nuclear factor NF-κB and phosphor-ERK in the cytoplasm. Hong et al., 2007; and Hsu et al., 2005, *Biochem Biophys Res Commun*, 327, 415-23.

Zfra may also participate in cell death regulation via the mitochondrial pathway. Dudekula et al., 2010, *Aging* (Albany N.Y.), 2, 1023-9; and Hsu et al., (2008) *Cell Signal*, 20, 1303-12. Overexpression of Zfra induced cell death, while the S8G-Zfra mutant could not induce cell death, suggesting that Serb phosphorylation is essential for Zfra translocation to the mitochondria, and is important for Zfra-induced cell death. Zfra blocks WOX1-induced cytochrome c release from the mitochondria, and induces apoptosis through dissipation of mitochondrial membrane potential (MMP), indicating a novel death regulation in mitochondria pathway. Dudekula et al., 2010; and Hsu et al., 2008.

SUMMARY OF THE INVENTION

The present disclosure is based on the unexpected discovery that Zfra activates a specific population of immune cells, which exhibits therapeutic effects against cancer.

Accordingly, one aspect of the present disclosure provides a method comprising: culturing immune cells in vitro in a medium that comprises (a) a peptide comprising the amino acid sequence of RRSSSCK (SEQ ID NO:1) to produce an immune cell population that comprises anti-cancer Z cells. In some examples, the medium further comprises CI-4AS-1 or Blebbistatin.

In some embodiments, the method may further comprise isolating Z cells from the immune cell population. In other embodiments, the method may further comprise administering an effective amount of the immune cell population that comprises anti-cancer Z cells to a subject having, suspected of having, or at risk for cancer (e.g., melanoma, breast cancer, prostate cancer, or lung cancer).

In any of the methods described herein, the peptide may comprise the amino acid sequence of SEQ ID NO:2. In some examples, the immune cells are spleen cells (e.g., human spleen cells), which may be autologous.

In another aspect, the present disclosure provides an immune cell population (e.g., an immune cell population prepared by an in vitro process as described herein), comprising anti-cancer Z cells, wherein the immune cell population is an in vitro cultured cell population. In some examples, the immune cell population may comprise at least 20% anti-cancer Z cells.

In some embodiments, the immune cell population can be prepared by a process comprising: culturing immune cells in vitro in a medium that comprises a peptide comprising the amino acid sequence of RRSSSCK (SEQ ID NO:1), and optionally CI-4AS-1, Blebbistatin, or a combination thereof, to produce the immune cell population, which comprises anti-cancer Z cells. In some examples, the immune cells are spleen cells.

In yet another aspect, the present disclosure provides a method for treating cancer, comprising administering to a subject in need thereof an effective amount of anti-cancer Z cells (e.g., autologous Z cells). In some examples, the subject is a human patient having, suspected of having, or at risk for cancer (e.g., melanoma, breast cancer, prostate cancer, or lung cancer). In some examples, the anti-cancer Z cells are prepared by incubating immune cells (e.g., spleen cells such as human spleen cells) with a peptide comprising the amino acid sequence of RRSSSCK (SEQ ID NO:1), e.g., a peptide comprises the amino acid sequence of SEQ ID NO:2. In one example, the immune cells are incubated with the peptide in the presence of CI-4AS-1, Blebbistatin, or a combination thereof.

Also within the scope of the present disclosure are (a) pharmaceutical compositions comprising any of the Z-cell containing immune cell populations as described herein for use in treating cancer, such as melanoma, breast cancer, prostate cancer, or lung cancer; and (b) use of the Z-cell containing immune cell population in manufacturing a medicament for the treatment cancer.

The details of one or more embodiments of the invention are set forth in the description below. Other features or advantages of the present invention will be apparent from the following drawings and detailed description of several embodiments, and also from the appended claims.

DETAILED DESCRIPTION OF THE INVENTION

Figure 1:
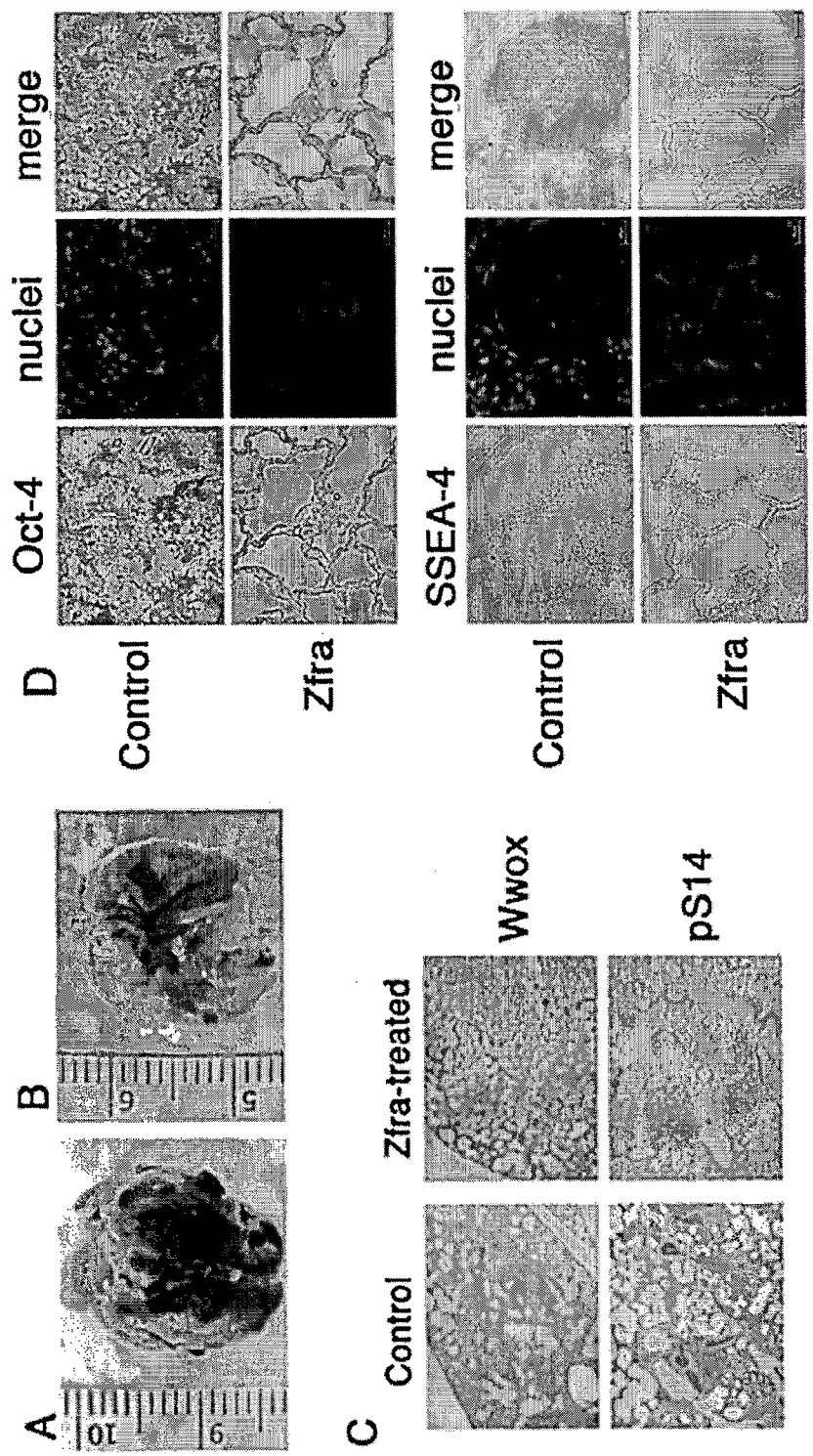
FIG. 1 includes photos showing that Zfra suppresses melanoma B16F10 metastasis to the lung and cancer stemness. BALB/c mice were pre-injected with sterile MilliQ water or Zfra4-10 (1 mM in 100 μl sterile water) in 3 consecutive weeks. Post-treatment for a week, these mice were inoculated with melanoma B16F10 cells via tail veins ($2 \times 10^5$ cells in 100 μl PBS). Control mice died 50 days later, and Zfra-treated mice were alive and sacrificed for examination. A: Shown on the lung surface are the metastatic tumor foci as dark areas in control mice. B: Metastasis was not found in Zfra-treated mice. No metastases were found in other organs in both mice. C: Zfra suppressed Ser14 phosphorylation of WWgre (or Wwox) in the lung of Zfra treated mice (~65% suppression). The Wwox protein levels were not suppressed. D: Zfra suppressed the stemness of B16F10 cells in the lung (using the pluripotent Oct-4 and SSEA-4 as markers).

The present disclosure is based on the unexpected discoveries that Zfra, either in a truncated form or full-length, activated a specific immune cell population (Z cells), which exhibited anti-cancer effects (e.g., inhibit cancer cell growth and block cancer cell metastasis). For example, when immune competent BALB/c mice or immune deficient nude and NOD-SCID mice were pre-injected with synthetic full length Zfra$_{1-31}$ or truncated Zfra$_{4-10}$ peptides via tail vein, these mice developed resistance against the growth of many types of cancer cells on their skin (65-100% suppression). Further, spleen cells treated with Zfra$_{1-31}$ or truncated Zfra$_{4-10}$ peptide produced a specific immune cell population (Z cells), which successfully inhibited cancer cell growth when injected into both immune competent and immune deficient mice.

Conventional immunotherapy methods often rely on immune cells that are specific to cancer cell antigens and target only the cancer population that express the specific cancer antigen. By contrast, Z cells as described herein, which are activated by Zfra peptides, can essentially memorize and attack cancer cells in a cancer-antigen independent manner. Thus, the Z cells as described herein can be used in treat all types of cancer.

Accordingly, described herein are immune cell populations containing Z cells, method for preparing such Z cells via, e.g., in vitro culturing in the presence of a Zfra peptide, and methods of using such cells in cancer treatment.

Anti-Cancer Z Cells and Methods for Preparing Such

"Z cells," as used herein, refer to a population of cells such as immune cells that express hyaluronidase-2 (Hyal-2$^+$), does not express one or more B-cell and/or T cell surface markers (e.g., CD3$^-$ and CD19$^-$), and are reactive to a Zfra peptide such as those described herein (e.g., capable of binding to the Zfra peptide). For example, Z cells can be Hyal-2$^+$, CD3$^-$, CD19$^-$, and capable of binding to a Zfra peptide (e.g., Zfra$_{4-10}$ or Zfra$_{1-31}$). Such immune cell populations can be activated in the presence of a Zfra peptide as described herein. In some examples, the immune cell population may containing at least 20% Z cells (e.g., 30%, 40%, 50%, 60%, 70%, 80%, 90%, 95%, or above).

Hyal-2 is an anchor protein located on the outer cell membrane via the glycosylphosphatidyl-inositol (GPI) linkage. It was found that HYAL-2 is a receptor of transforming growth factor beta 1 (TGF-β1). Hsu et al., *J. Biol. Chem.*, 284:16049-16059; 2009. As an example, the amino acid sequence of human Hyal-2 is provided below (SEQ ID NO:3):

```
mragpgptvt lalvlayswa melkptappi ftgrpfvvaw dvptqdcgpr lkvpldlnaf dvqaspnegf vnqnitifyr drlglyprfd sagrsvhggv pqnvslwahr kmlqkrvehy irtqesagla vidwedwrpv wvrnwqdkdv yrrlsrqlva srhpdwppdr ivkqaqyefe faaqqfmlet lryvkavrpr hlwgfylfpd cynhdyvqnw esytgrcpdv evarndqlaw lwaestalfp svyldetlas srhgrnfvsf rvqealrvar thhanhalpv yvftrptysr rltglsemdl istigesaal gaagvilwgd agyttstetc qylkdyltrl lvpyvvnvsw atqycsraqc hghgrcvrrn psastflhls tnsfrlvpgh apgepqlrpv gelswadidh lgthfrcqcy lgwsgeqcqw dhrqaaggas eawagshlts llalaalaft wtl
```

B cell-specific and T cell-specific surface markers are well known in the art. Exemplary B-cell markers include, but are not limited to, CD19, CD20, CD24, CD27, CD28, CD34, CD38, BCMA/TNFRSF17, and ENPP-1. Exemplary T cell markers include, but are not limited to CD3, CD4, CD8, CD25, CD26, CD27, CD28, CD30, CD40L, CD71, CD154, and CD134. The Z cells described herein are negative in one or more of B cell-specific surface markers (e.g., CD19 and/or CD20) and one or more T cell-specific surface markers (e.g., CD3, CD4, and/or CD8).

The Z cells described herein can be identified based on their surface presence of one or more B-cell and T-cell markers and their reactivity to a Zfra peptide as described herein via routine technology (e.g., FACS staining). For example, an agent (e.g., antibody) specific to Hyal-2 and one or more of the B-cell/T-cell markers (CD3 and CD19) can be used to determine whether a candidate cell express such B-cell/T-cell markers and Hyal-2. Further, a Zfra peptide conjugated with a detectable label (directly or indirectly) can be used to identify cells that are capable of binding to the Zfra peptide.

The Z-cell-containing population can be prepared by in vitro activation by a Zfra peptide. Zinc-finger like protein that regulates apoptosis (Zfra) is a is a 31-amino-acid peptide containing two cysteines and one histidine and is similar to C2H2-type zinc finger proteins. (Hsu et al., 2005, *Biochem Biophys Res Commun*, 327, 415-23; Hong et al., 2007 *BMC Mol Biol*, 8, 50; Hsu et al., 2008, *Cell Signal*, 20, 1303-12; and Dudekula et al., 2010, *Aging* (Albany N.Y.), 2, 1023-9.) The amino acid sequence of the full-length Zfra is:

NH-MSSRRSSSCKYCEQDFRAHTQKNAATPFLAN-COOH (SEQ ID NO:2)

The serine residue in boldface is the serine phosphorylation sites Ser8 (S8), which was found to be essential to the activity of Zfra in regulating apoptosis. (Hong et al., 2007; Hsu et al., 2005). It was shown in the present study that a fragment of the full-length Zfra, RRSSSCK (Zfra$_{4-10}$, SEQ ID NO:1) is sufficient to induce Z cell activation both in vivo and in vitro. See also WO2013/009948, which is incorporated by reference herein.

The term "a Zfra peptide" refers to a peptide comprising the amino acid sequence of SEQ ID NO:1 (Zfra$_{4-10}$). A Zfra peptide may consist of up to 50 amino acid residues (e.g., up to 45, 40, 35, 30, 25, or 20 amino acid residues). In some examples, a Zfra peptide as described herein may comprise SEQ ID NO:1 and share at least 75% sequence identity (e.g., 80%, 85%, 90%, 95%, or higher) as compared with the full-length Zfra (SEQ ID NO:2). In one example, the Zfra peptide consists of SEQ ID NO:2.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

Any of the Zfra peptides as described herein can be used to activate the production of Z cells both in vivo and in vitro. In some examples, an in vitro culturing process can be performed to produce an immune cell population that contain Z cells as follows. A population of immune cells, such as spleen cells, blood cells (e.g., peripheral blood mononuclear cells), and bone marrow cells, can be collected from a suitable source, e.g., a healthy donor such as a human donor via routine practice. In some examples, the immune cell population may contain B cells. In some examples, the population of immune cells may obtained from a cancer patient, to whom an adoptive cell transfer immunotherapy is later performed. See descriptions below.

The population of immune cells are cultured in vitro in a suitable medium that contains a suitable concentration of a Zfra peptide (e.g., 20 μM to 200 μM, such as 40 μM to 150 μM, 50 μM to 120 μM; 50 μM to 100 μM; 100 μM to 150 μM; or 150 μM to 200 μM) under suitable conditions for a suitable period of time to induce production of anti-cancer Z cells. In some examples, the culture medium may further comprise CI-4AS-1, Blebbistatin, or a combination thereof. For example, immune cells such as spleen cells, bone marrow cells, or blood cells can be isolated from a suitable donor. If needed, the cells can be resuspended in a suitable medium (e.g., an RPMI medium), which may be supplemented with fetal bovine serum at a suitable concentration (e.g., 10%). The cells may be cultured for a suitable period of time (e.g., overnight) in an incubator under suitable conditions (e.g., at 37° C. with 5% $CO_2$/atmosphere). The cells can then be treated by a Zefra peptide (e.g., Zfra$_{1-31}$ or Zfra$_{4-10}$) at a suitable concentration as indicated herein for a suitable period of time (e.g., 16-24 hours). The cells can then be stained with a Zfra peptide conjugated to a detectable label (e.g., TMR-Zfra, which is Zfra1-31 labeled with red fluorescent tetramethylrodamine) to identify Z cells. Positive cells can be collected using a cell sorting machine.

In some examples, Z cells may be enriched from the Z-cell-containing immune cell population as described herein, e.g., by cell sorting using an antibody that binds to a Z-cell surface marker (e.g., Hyal-2) or using a Zfra peptide. The Z-cell-enriched cell population thus obtained may contain at least 20% Z cells (e.g., 30%, 40%, 50%, 60%, 70%, 80%, 90%, or 95%).

Any of the immune cell populations that contain Z cells may be used directly in cancer treatment. Alternatively, the cells may be frozen (cryopreserved). Thus, the method may include the further step of cryopreserving the cells. The cells are preferably frozen in a cryopreservative, which is compatible with ultimately thawing the frozen cells and, after optionally washing the cells to remove the cryopreservative, the immune cells, including Z cells, may retain at least 25% cell viability (such as based on culture efficiency), and more preferably at least 50%, 60%, 70%, 80% or even at least 90% cell viability.

Anti-Cancer Adoptive Cell Transfer Immunotherapy Using Z Cells

The Z cells as described herein can be used in cancer treatment. To practice such a treatment, an effective amount of an immune cell population that contains Z cells can be transferred to a subject in need of the treatment in any physiologically acceptable excipient comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996. Choice of the cellular excipient and any accompanying elements of the composition will be adapted in accordance with the route and device used for administration. The cells may be introduced by injection, catheter, or the like. The cells may be frozen at liquid nitrogen temperatures and stored for long periods of time, being capable of use on thawing.

The pharmaceutical preparations of cells described herein may comprise at least about 1,000; 2,000; 3,000; 4,000; 5,000; 6,000; 7,000; 8,000; or 9,000 Z cells. The pharmaceutical preparations of cells may comprise at least about $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, or $5 \times 10^8$ Z cells. In some examples, the pharmaceutical preparations of Z cells may comprise at least about $1 \times 10^2$-$1 \times 10^3$, $1 \times 10^2$-$1 \times 10^4$, $1 \times 10^4$-$1 \times 10^5$, or $1 \times 10^3$-$1 \times 10^6$ Z cells.

In the aforesaid pharmaceutical preparations and compositions, the number of Z cells or concentration cells may be determined by counting viable cells and excluding non-viable cells. For example, non-viable cells may be detected by failure to exclude a vital dye (such as Trypan Blue), or using a functional assay (such as the ability to adhere to a culture substrate, etc.). Additionally, the number of cells or concentration of cells may be determined by counting cells that express one or more cell markers and/or excluding cells that express one or more markers indicative of a cell type other than the desired cell type.

The Z cells or immune cell population comprising such may be formulated with a pharmaceutically acceptable carrier. The carrier in the pharmaceutical composition must be "acceptable" in the sense that it is compatible with the cells in the composition, and preferably, capable of stabilizing the cells and not deleterious to the subject to be treated. For example, the Z cells or immune cell population may be administered alone or as a component of a pharmaceutical formulation. The subject cells may be formulated for administration in any convenient way for use in medicine. Pharmaceutical preparations suitable for administration may comprise the Z cells or immune cell population, in combination with one or more pharmaceutically acceptable sterile isotonic aqueous or non-aqueous solutions (e.g., balanced salt solution (BSS)), dispersions, suspensions or emulsions, or sterile powders, which may be reconstituted into sterile injectable solutions or dispersions just prior to use, which may contain antioxidants, buffers, bacteriostats, solutes or suspending or thickening agents.

An effective amount of the Z cells or an immune cell population containing such as described herein may be administered into a subject in need of the treatment (e.g., a human patient having cancer, suspected of having cancer, or at risk for developing cancer) via suitable route. Such a subject may be identified via routine medical practice. In some examples, the subject is a cancer patient having or at risk for cancer metastasis.

The term "cancer" as used herein refers to cells having the capacity for autonomous growth, i.e., an abnormal state or condition characterized by rapidly proliferating cell growth. It is meant to include all types of cancerous growths or oncogenic processes, metastatic tissues or malignantly transformed cells, tissues, or organs, irrespective of histopathologic type or stage of invasiveness. Exemplary types of cancer that can be treated by the method described herein include, but are not limited to, melanoma, breast cancer, prostate cancer, and lung cancer (e.g., small-cell lung cancer or non-small cell lung cancer).

The term "treating" as used herein refers to the application or administration of a composition including the Z cells described herein to a subject, who has a cancer, a symptom of cancer, or a predisposition toward cancer, with the purpose to cure, heal, alleviate, relieve, alter, remedy, ameliorate, improve, or affect the disease, the symptoms of the disease, or the predisposition toward the disease.

"An effective amount" as used herein refers to the amount of Z cells required to confer a desired therapeutic effect on the subject, either alone or in combination with one or more other active agents (e.g., anti-cancer agent). Effective amounts vary, as recognized by those skilled in the art, depending on route of administration, excipient usage, and co-usage with other active agents. The desired therapeutic effect may include inhibit or prevent cancer cell growth, reduced the risk for cancer development, and/or block or inhibit cancer cell metastasis in the subject who is treated with the method described herein. This may involve only slowing the progression of the disease temporarily, although more preferably, it involves halting the progression of the disease permanently. This can be monitored by routine methods or can be monitored according to diagnostic methods of the invention discussed herein. The desired response to treatment of the disease or condition also can be delaying the onset or even preventing the onset of the disease or condition.

Such amounts will depend, of course, on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

In some embodiments, the anti-cancer Z cells described herein can be combined with one or more other anti-cancer therapy, including surgery, chemotherapy, and/or radiotherapy. In some examples, the Z cells can be co-administered with one or more other anti-cancer agents. The term "co-administration" is meant to refer to a combination therapy by any administration route, in which two or more agents are administered to a subject in need of the treatment. Co-administration of agents may also be referred to as combination therapy or combination treatment. The agents may be in the same dosage formulations or separate formulations. For combination treatment with more than one active agent, where the active agents are in separate dosage formulations, the active agents can be administered concurrently, or they each can be administered at separately staggered times. The agents may be administered simultaneously or sequentially (e.g., one agent may directly follow administration of the other or the agents may be give episodically, e.g., one can be given at one time followed by the other at a later time, e.g., within a week), as long as they are given in a manner sufficient to allow both agents to achieve effective concentrations in the body. The agents may also be administered by different routes, e.g., one agent may be administered intravenously while a second agent is administered intramuscularly or orally. Thus, the anticancer agent may be administered prior to, concomitant with, or after the administration of the Z cells. Co-administrable agents also may be formulated as an admixture, as, for example, in a single formulation or single tablet. These formulations may be parenteral or oral, such as the formulations described, e.g., in U.S. Pat. Nos. 6,277,384; 6,261, 599; 5,958,452 and PCT publication No. WO 98/25613, each hereby incorporated by reference.

Examples of anti-cancer agent include, but are not limited to, chemotherapeutic agents, growth inhibitory agents, cytotoxic agents, agents used in radiation therapy, anti-angiogenesis agents, apoptotic agents, anti-tubulin agents, and other-agents to treat cancer such as, anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the targets molecule and other bioactive and organic chemical agents.

Examples of anti-breast cancer drugs include, but not limited to, Abitrexate (Methotrexate), Abraxane (Paclitaxel Albumin-stabilized Nanoparticle Formulation), Ado-Trastuzumab Emtansine, Adriamycin PFS (Doxorubicin Hydrochloride), Adriamycin RDF (Doxorubicin Hydrochloride), Adrucil (Fluorouracil), Afinitor (Everolimus), Anastrozole, Aredia (Pamidronate Disodium), Arimidex (Anastrozole), Aromasin (Exemestane), Capecitabine, Clafen (Cyclophosphamide), Cyclophosphamide, Cytoxan (Cyclophosphamide), Docetaxel, Doxorubicin Hydrochloride, Efudex (Fluorouracil), Ellence (Epirubicin Hydrochloride), Epirubicin Hydrochloride, Everolimus, Exemestane, Fareston (Toremifene), Faslodex (Fulvestrant), Femara (Letrozole), Fluoroplex (Fluorouracil), Fluorouracil, Folex (Methotrexate), Folex PFS (Methotrexate), Fulvestrant, Gemcitabine Hydrochloride, Gemzar (Gemcitabine Hydrochloride), Goserelin Acetate, Herceptin (Trastuzumab), Ixabepilone, Ixempra (Ixabepilone), Kadcyla (Ado-Trastuzumab Emtansine), Lapatinib Ditosylate, Letrozole, Megace (Megestrol Acetate), Megestrol Acetate, Methotrexate, Methotrexate LPF (Methotrexate), Mexate (Methotrexate), Mexate-AQ (Methotrexate), Neosar (Cyclophosphamide), Nolvadex (Tamoxifen Citrate), Novaldex (Tamoxifen Citrate), Paclitaxel, Paclitaxel Albumin-stabilized Nanoparticle Formulation, Pamidronate Disodium, Perjeta (Pertuzumab), Pertuzumab, Tamoxifen Citrate, Taxol (Paclitaxel), Taxotere (Docetaxel), Trastuzumab, Toremifene, Tykerb (Lapatinib Ditosylate), Xeloda (Capecitabine), and Zoladex (Goserelin Acetate).

Anti-melanoma drugs include Aldesleukin, Dabrafenib, Dacarbazine, DTIC-Dome (Dacarbazine), Intron A (Recombinant Interferon Alfa-2b), Ipilimumab, Mekinist (Trametinib), Peginterferon Alfa-2b, PEG-Intron (Peginterferon Alfa-2b), Proleukin (Aldesleukin), Recombinant Interferon Alfa-2b, Sylatron (Peginterferon Alfa-2b), Tafinlar (Dabrafenib), Trametinib, Vemurafenib, Yervoy (Ipilimumab), and Zelboraf (Vemurafenib).

Drugs for treating non-small cell lung cancer include Abitrexate (Methotrexate), Abraxane (Paclitaxel Albumin-stabilized Nanoparticle Formulation), Afatinib Dimaleate, Alimta (Pemetrexed Disodium), Avastin (Bevacizumab), Carboplatin, Cisplatin, Crizotinib, Docetaxel, Erlotinib Hydrochloride, Folex (Methotrexate), Folex PFS (Methotrexate), Gefitinib, Gilotrif (Afatinib Dimaleate), Gemcitabine Hydrochloride, Gemzar (Gemcitabine Hydrochloride), Iressa (Gefitinib), Methotrexate, Methotrexate LPF (Methotrexate), Mexate (Methotrexate), Mexate-AQ (Methotrexate), Paclitaxel, Paclitaxel Albumin-stabilized Nanoparticle Formulation, Paraplat (Carboplatin), Paraplatin (Carboplatin), Pemetrexed Disodium, Platinol (Cisplatin), Platinol-AQ (Cisplatin), Tarceva (Erlotinib Hydrochloride), Taxol (Paclitaxel), Taxotere (Docetaxel), and Xalkori (Crizotinib).

Drugs for treating small-cell lung cancer include Abitrexate (Methotrexate), Etopophos (Etoposide Phosphate), Etoposide, Etoposide Phosphate, Folex (Methotrexate), Folex PFS (Methotrexate), Hycamtin (Topotecan Hydrochloride), Methotrexate, Methotrexate LPF (Methotrexate), Mexate (Methotrexate), Mexate-AQ (Methotrexate), Toposar (Etoposide), Topotecan Hydrochloride, and VePesid (Etoposide).

Anti-prostate cancer drugs include Abiraterone Acetate, Bicalutamide, Cabazitaxel, Casodex (Bicalutamide), Degarelix, Denosumab, Docetaxel, Enzalutamide, Jevtana (Cabazitaxel), Leuprolide Acetate, Lupron (Leuprolide Acetate), Lupron Depot (Leuprolide Acetate), Lupron Depot-3 Month (Leuprolide Acetate), Lupron Depot-4 Month (Leuprolide Acetate), Lupron Depot-Ped (Leuprolide Acetate), Prednisone, Prolia (Denosumab), Provenge (Sipuleucel-T), Radium 223 Dichloride, Sipuleucel-T, Taxotere (Docetaxel), Viadur (Leuprolide Acetate), Xgeva (Denosumab), Xofigo (Radium 223 Dichloride), Xtandi (Enzalutamide), and Zytiga (Abiraterone Acetate).

Any of the above-listed drugs can be co-used with the Z-cells described herein for treating the target cancer. The co-use of a Zfra peptide as described herein and CI-4AS-1, Blebbistatin, or a combination thereof is also within the scope of this disclosure.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

Truncated Zfra Peptide Suppresses Cancer Metastasis and Stemness

BALB/c mice were pre-injected with sterile MilliQ water or $Zfra_{4-10}$ (1 mM in 100 μl sterile water) once per week in three consecutive weeks. Following one week post-treatment, the mice were inoculated with melanoma B16F10 cells via tail veins ($2\times10^5$ cells in 100 μl PBS). Mice receiving the control died 50 days following inoculation of B16F10 cells, while $Zfra_{4-10}$-treated mice remained alive and were sacrificed for examination.

As shown in FIG. 1, $Zfra_{4-10}$ suppressed melanoma B16F10 metastasis to the lung, while the lung tissues of control mice displayed metastatic tumor foci (FIG. 1A vs. 1B). The suppression of metastasis in the treated mice correlated with inhibition of Ser14 phosphorylation of WWOX (FIG. 1C). Importantly, cancer cell stemness, as determined by the expression of pluripotent stem cell markers Oct-4 and SSEA-4, was blocked in the lungs of $Zfra_{4-10}$ treated mice (FIG. 1D). Thus, when WWOX phosphorylation at Ser14 is blocked by Zfra, cancer cell metastasis and stemness is prevented.

Example 2

Figure 2:
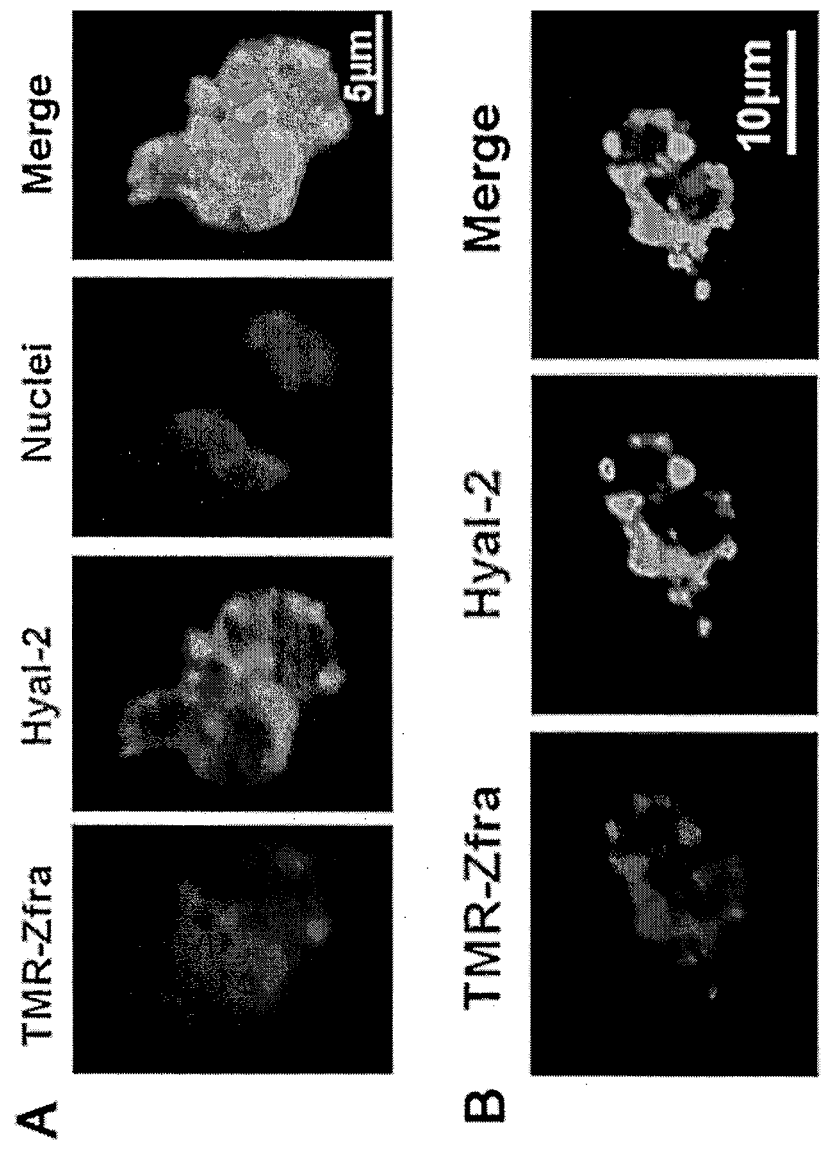
FIG. 2 includes photos showing the identification of Zfra$^+$ Hyal-2$^+$ spleen cells. A and B: Spleen cells of NOD-SCID mice were isolated and stained with synthesized peptide TMR-Zfra$_{1-31}$ and Hyal-2 (green fluorescence) antibody for 30 minutes on ice, and then fixed with 4% formaldehyde. Zfra bound to membrane hyaluronidase Hyal-2, as determined by epifluorescence and confocal microscopy. C: FRET analysis revealed the binding of Zfra to membrane Hyal-2.
Figure 2:
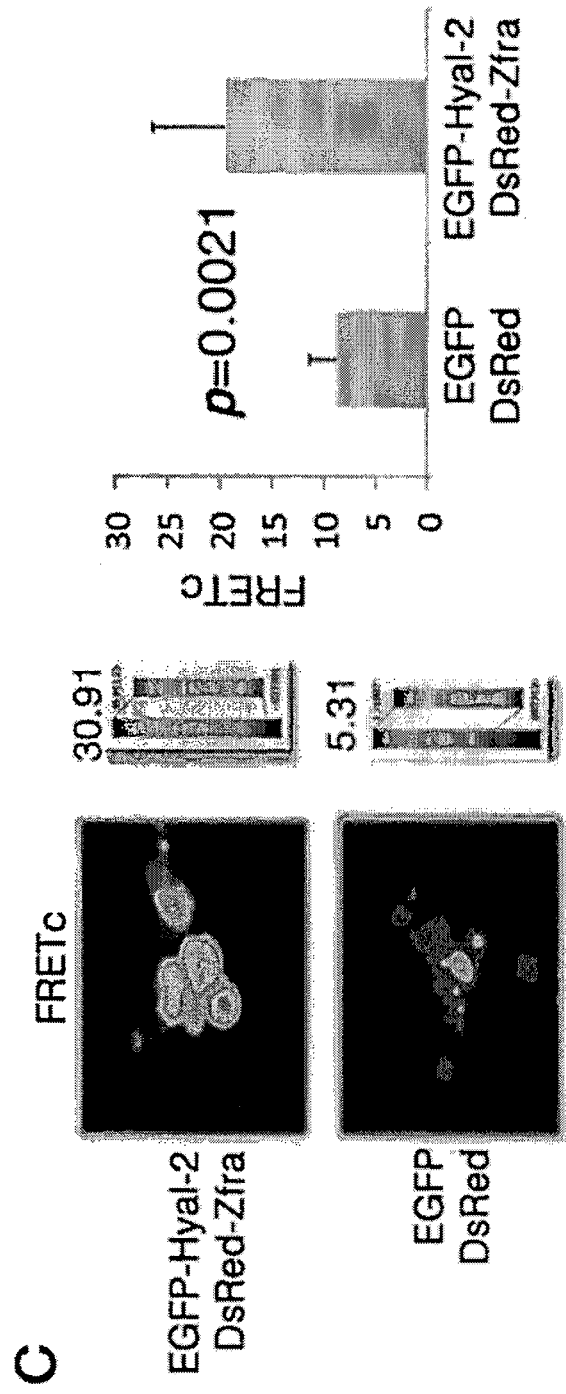

Isolation of Novel Zfra-Binding Hyal-2$^+$ Z Lymphocytes and their Down-Regulation in Tumor-Bearing Mice In this example, spleen cells were isolated from immune deficient NOD-SCID mice, which are deficient in T and B lymphocytes and NK cells. The isolated spleen cells were stained with antibody against Hyal-2 (green) and TMR-Zfra ($Zfra_{1-31}$ labeled with red fluorescent tetramethylrodamine) for 30 minutes on ice, and then fixed with 4% formaldehyde (FIG. 2). Confocal analysis revealed the colocalization of both proteins on the cell surface (FIG. 2A, B). Förster resonance energy transfer (FRET) analysis (Hong et al., 2009) showed the significant binding of EGFP-Zfra with DsRed-Hyal-2, as compared to the EGFP and DsRed controls (n=10; p<0.005; Student's t test) (FIG. 2C). These Hyal-2$^+$ Zfra$^+$ positive cells are interchangeably referred to as "Z cells," for cells interacting with Zfra.

Figure 3:
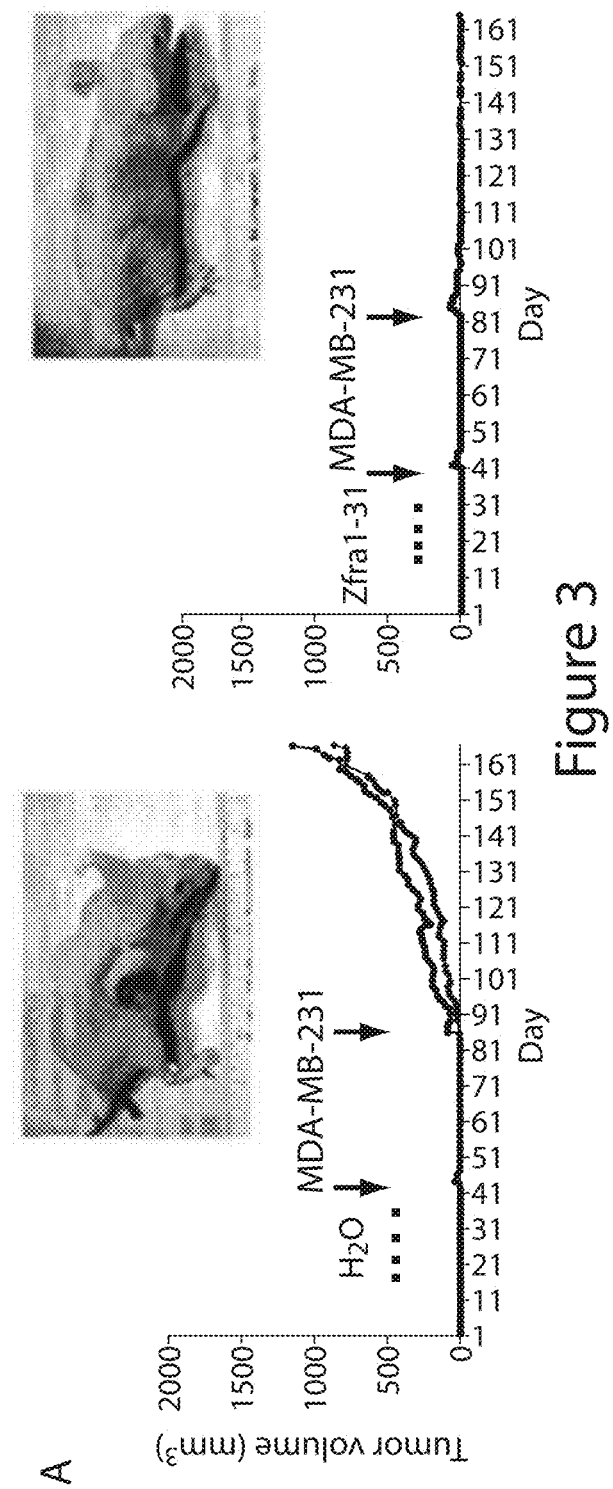
FIG. 3 is a diagram showing identification of Z spleen cells. (A) Nude mice were pre-injected with sterile MilliQ water or a mixture of Zfra1-31 (2 mM in 100 μl sterile water) in 4 consecutive weeks, followed by inoculating malignant breast MDA-MB-231 cells on both flanks 7 and 50 days later. Tumor sizes on both flanks (blue and red) were measured daily. (B and C) Zfra completely blocked B16F10 melanoma in BALB/c mice. These mice were sacrificed, and TMR-Zfra-positive spleen cells were isolated by cell sorting. TMR-Zfra-positive Z spleen cells were around 25% in Zfra-treated mice. Z cells do not exhibit T and B cell markers. In B16F10 melanoma-growing BALB/c mice, spleen Z cells dropped down to 3.3% or even lower. In untreated control mice, Z cells are around 25-29%.
Figure 3:
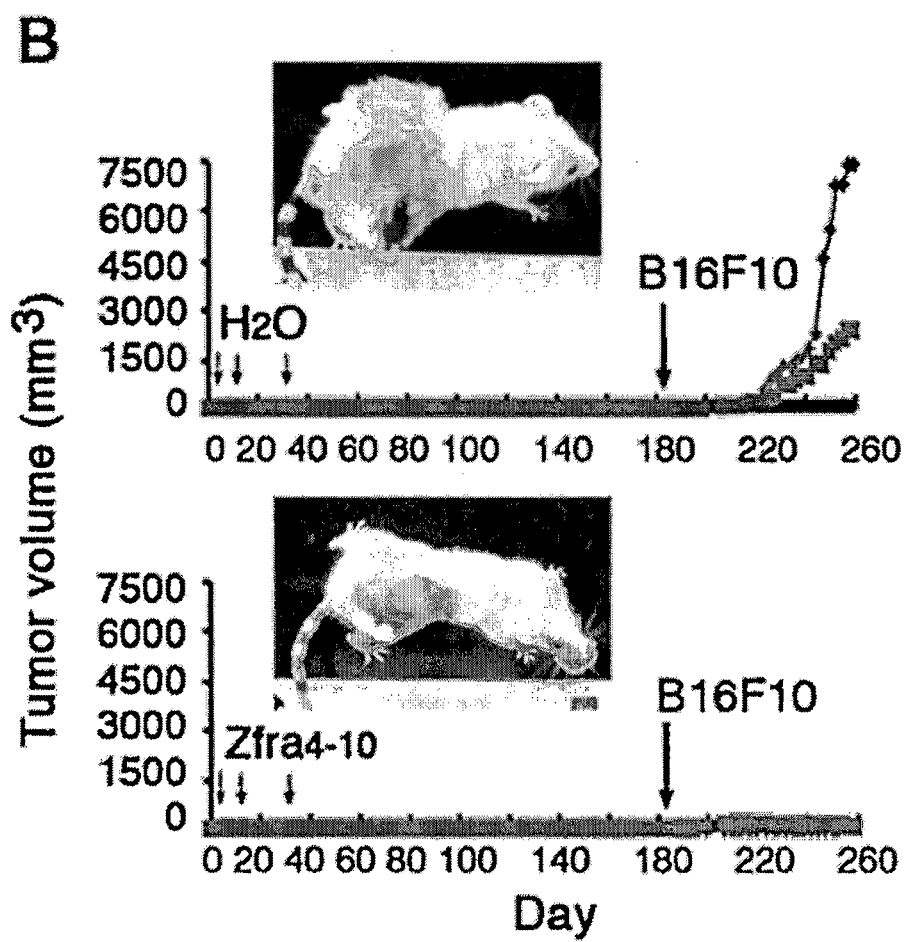
Figure 3:
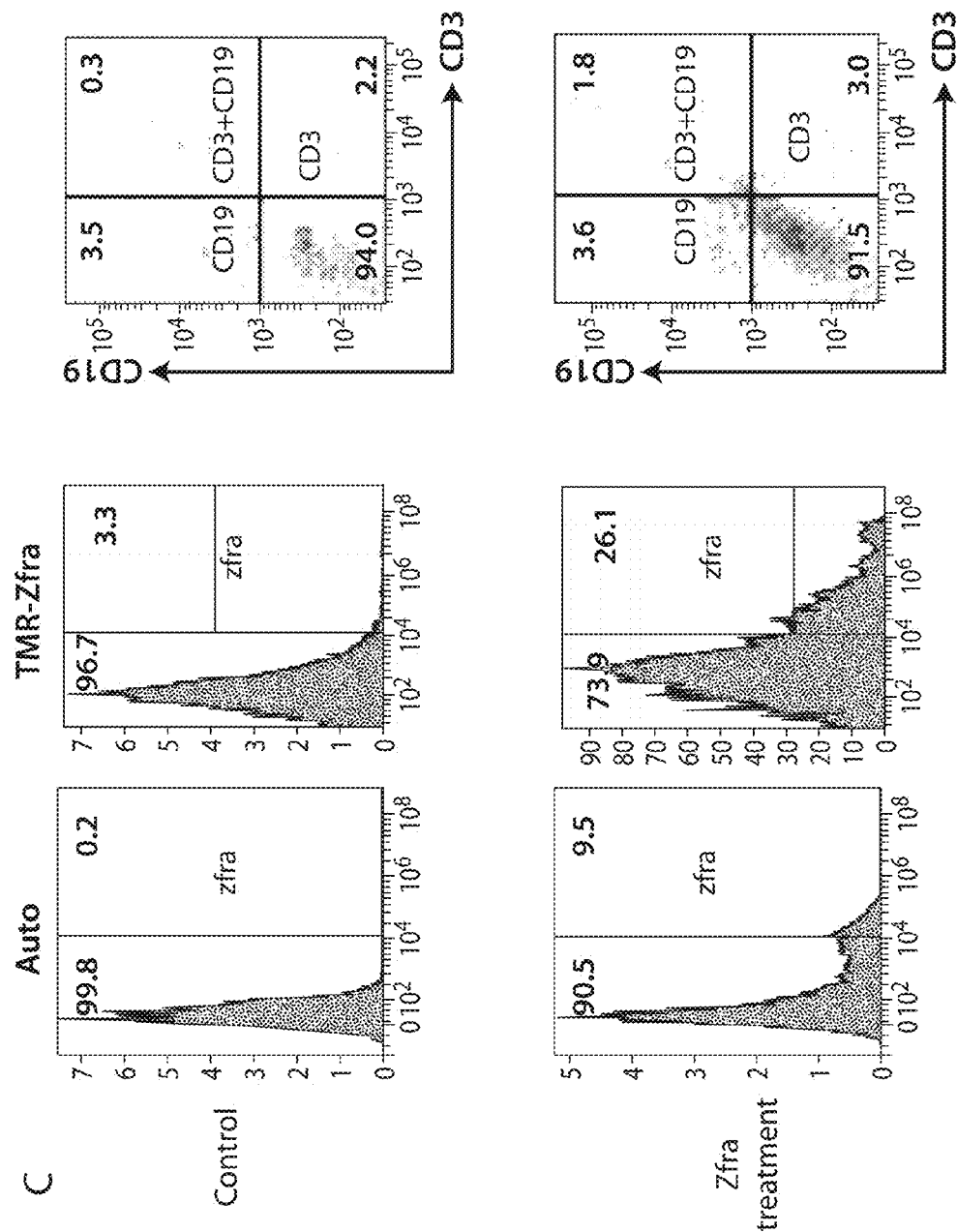

When immune deficient nude mice were pre-injected with the full-length $Zfra_{1-31}$ peptide once per week for 4 weeks, these mice resisted the growth of breast MDA-MB-231 xenografts (FIG. 3A). Similarly, the truncated $Zfra_{4-10}$ peptide prevented melanoma B16F10 growth in immune competent BALB/c mice (FIG. 3B).

Next, the levels of spleen Z cells in mice pre-treated with full-length $Zfra_{1-31}$ or control and inoculated with B16F10 melanoma cells were examined. B16F10-growing BALB/c mice had low levels of Z cells, which were 3.3% or lower (FIG. 3C). In contrast, Zfra-treated mice had 26.1% Z cells (FIG. 3C). Importantly, Z cells do not exhibit T and B cell markers, as determined using fluorescent CD3 and CD19 antibodies, respectively (FIG. 3C). These cells are Hyal-2 positive. The observations indicate that Z cells (e.g., Hyal-2 positive spleen cells) are depleted in mice having cancer growths, and that treatment with Zfra increases the number of Z cells in mice having cancer growths.

Example 3

Identification of Compounds which Increase the Anti-Cancer Efficacy of Z Cell Based Treatment In this example, more than 300 hundred compounds were screened for their activities in boosting Z cell function either alone or in combination with a Zfra peptide. From this collection of compounds, CI-4AS-1 (androgen receptor agonist) and (±)-Blebbistatin (inhibitor for non-muscle myosin II ATPase) were identified.

Figure 4A:
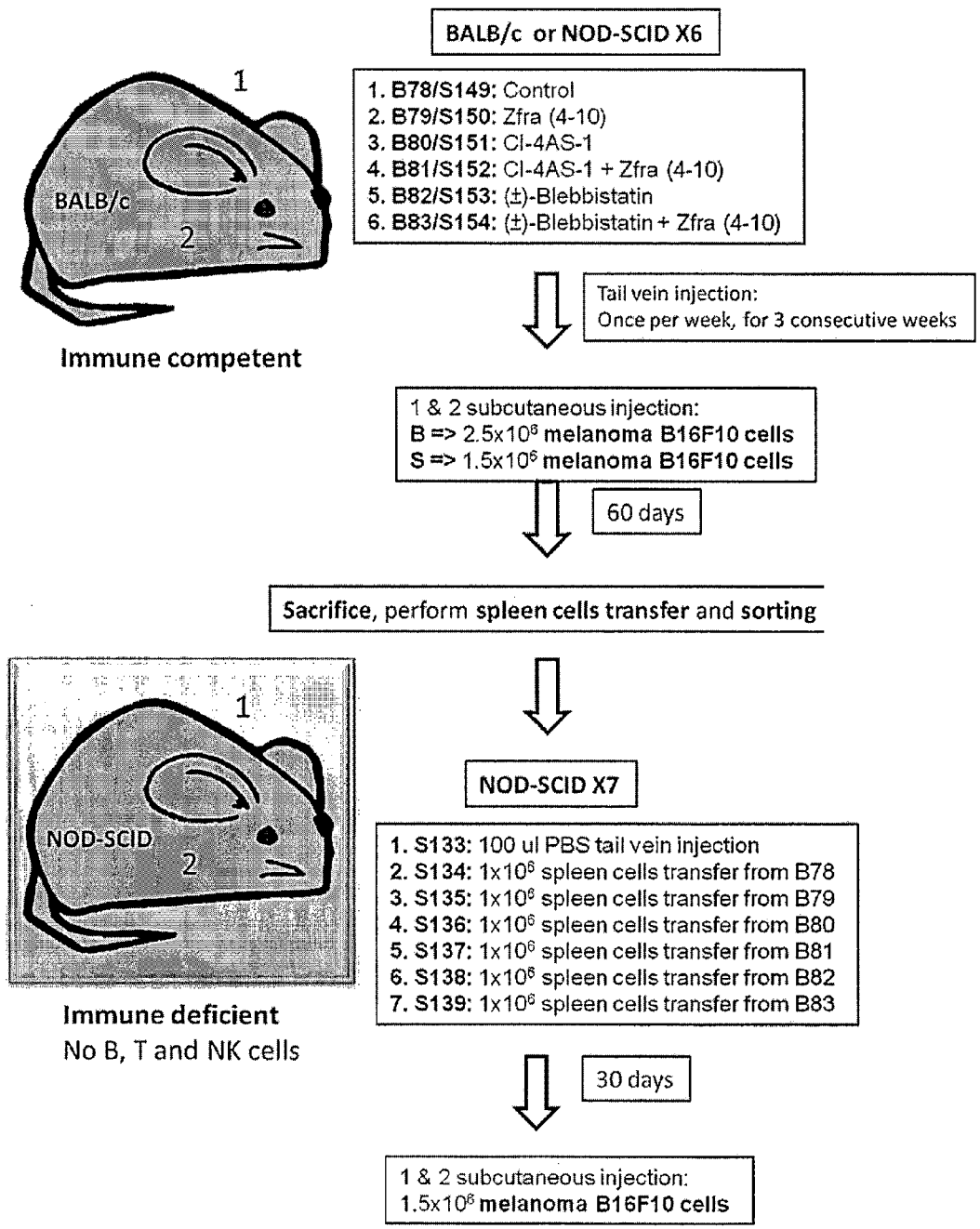
FIG. 4A is a diagram showing in vivo animal models design to test the anticancer efficacy of chemical drugs and "Z cells" activation. Immune competent BALB/c mice or immune deficient NOD-SCID mice were pre-injected with CI-4AS-1 or (±)-Blebbistatin with or without zinc finger-like Zfra$_{4-10}$ peptide once per week for 3 consecutive weeks, and then inoculated with 2.5×10$^6$ or 1.5×10$^6$ malignant melanoma B16F10 cells at both right and left flanks. After 60 days, spleen cells transferred were performed from BALB/c to NOD-SCID mice via tail veins injection. Thirty days later, the recipient mice were inoculated with 1.5×10$^6$ malignant melanoma B16F10 cells at both right and left flanks.

Next, Immune competent BALB/c mice or immune deficient NOD-SCID mice were pre-injected with CI-4AS-1 or (±)-Blebbistatin (suspended in dimethyl sulfoxide; DMSO), in the presence or absence of $Zfra_{4-10}$ peptide once per week for 3 consecutive weeks. These mice were then inoculated with $2.5 \times 10^6$ or $1.5 \times 10^6$ malignant melanoma B16F10 cells at both right and left flanks. Sixty days later, spleen cell transfer from donor BALB/c to recipient NOD-SCID mice was performed via tail vein injection. Thirty days later, the recipient mice were inoculated with $1.5 \times 10^6$ B16F10 cells at both right and left flanks. See FIG. 4A for a schematic model depicting the experimental approach.

Figure 4B:
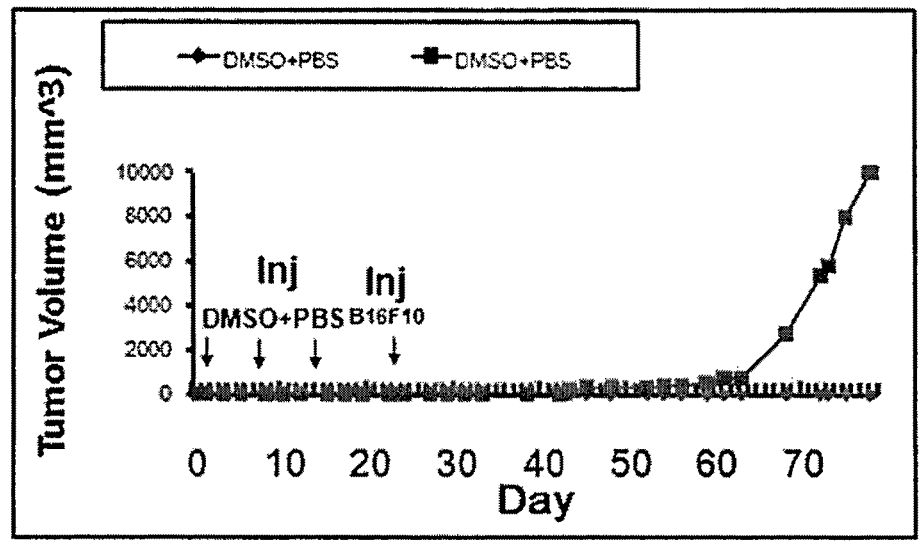
FIG. 4B includes charts showing that all treatments as indicated blocked the growth of B16F10 cells in BALB/c mice (mice B78-B83).
Figure 4B:
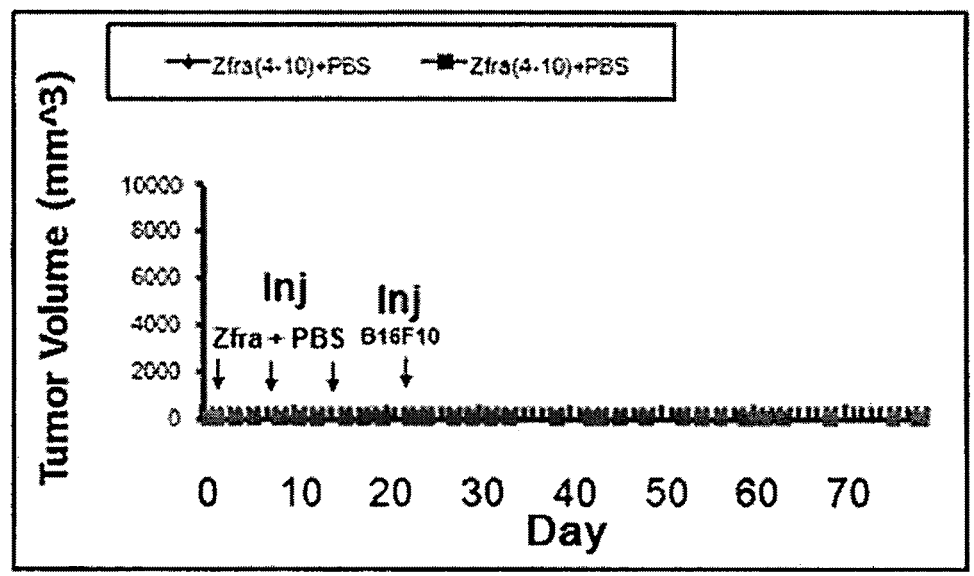
Figure 4B:
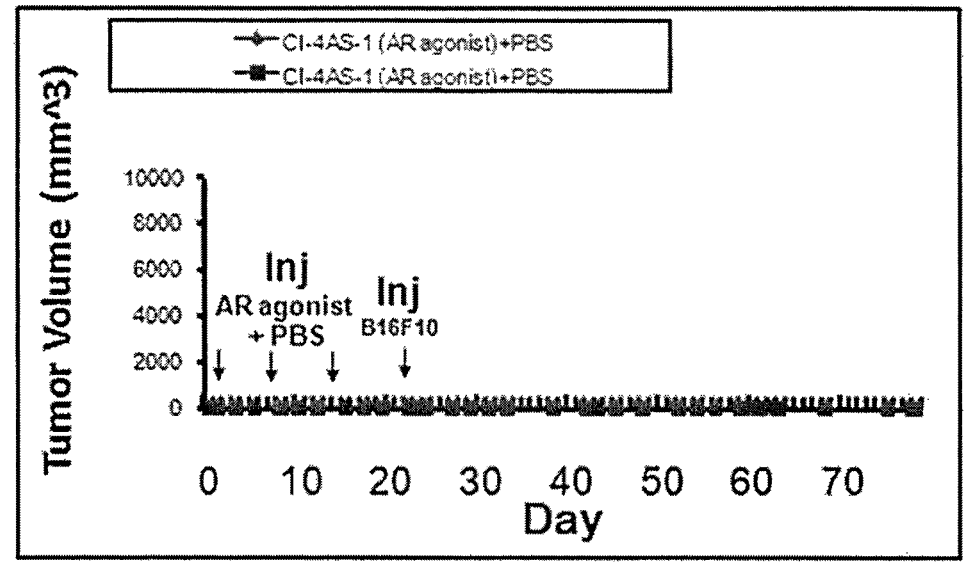
Figure 4B:
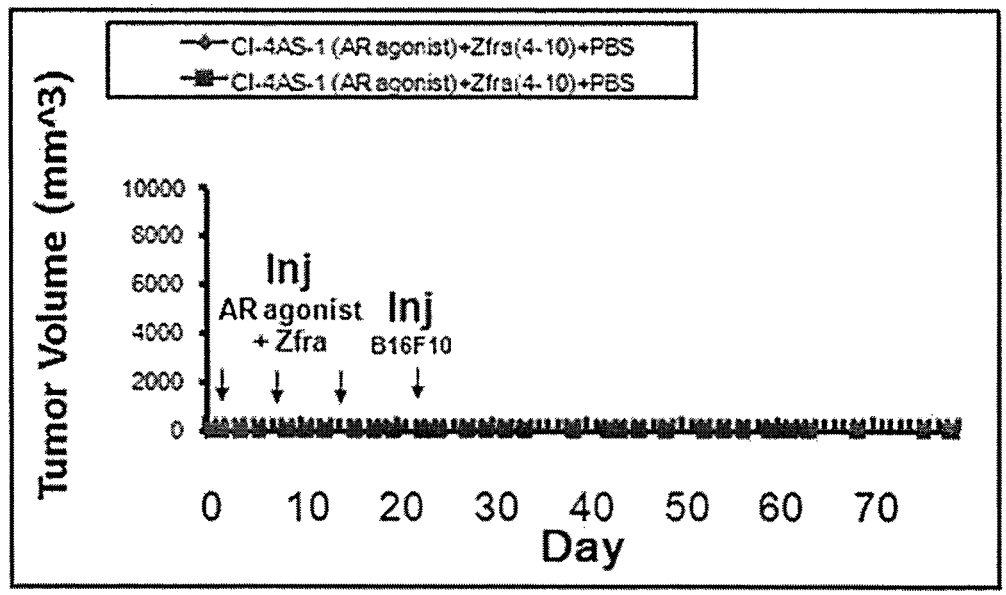
Figure 4B:
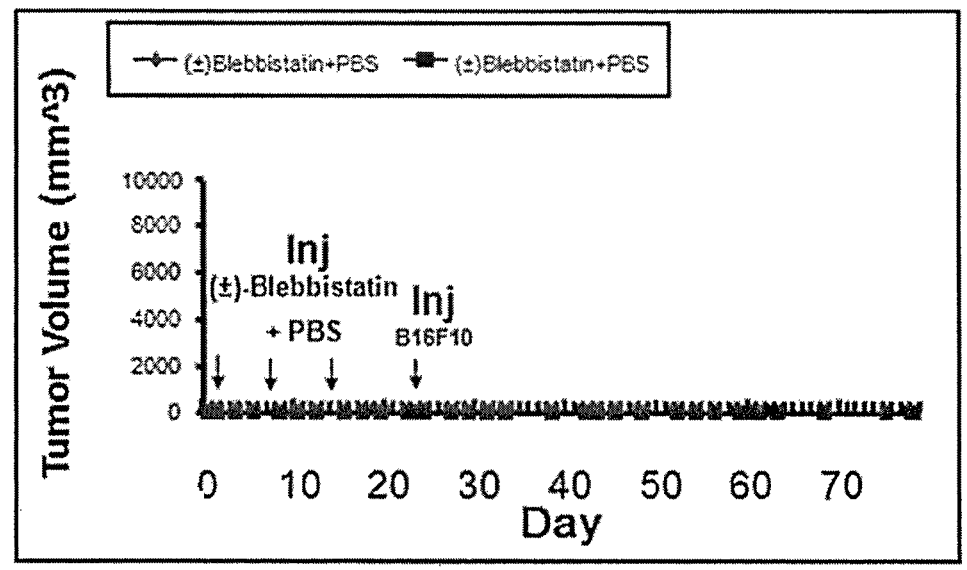
Figure 4B:
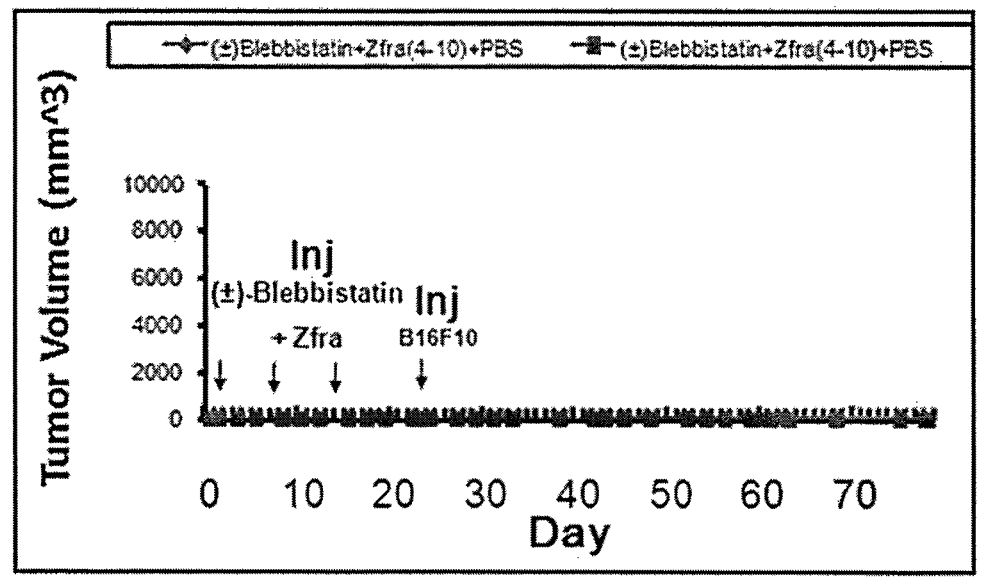
Figure 4C:
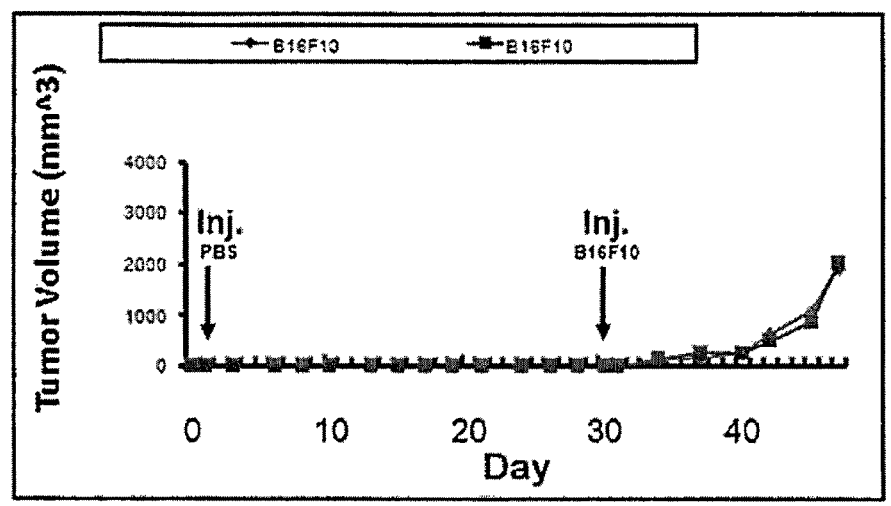
FIG. 4C includes chart showing that all treatments as indicated only slightly retarded the growth of B16F10 cells in NOD-SCID mice (mice S133-139).
Figure 4C:
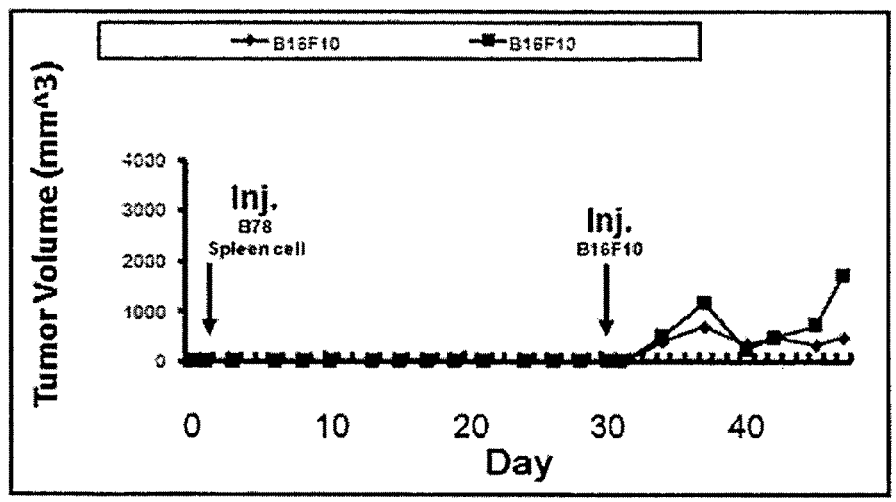
Figure 4C:
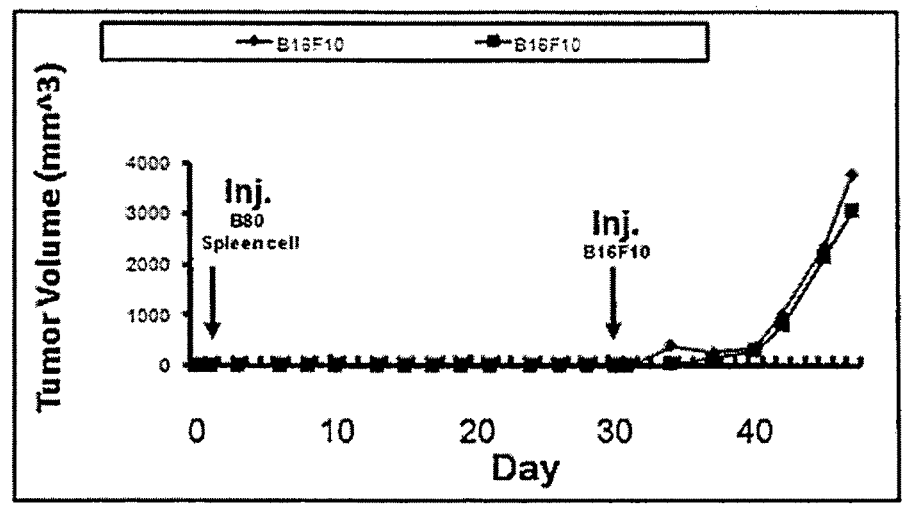
Figure 4C:
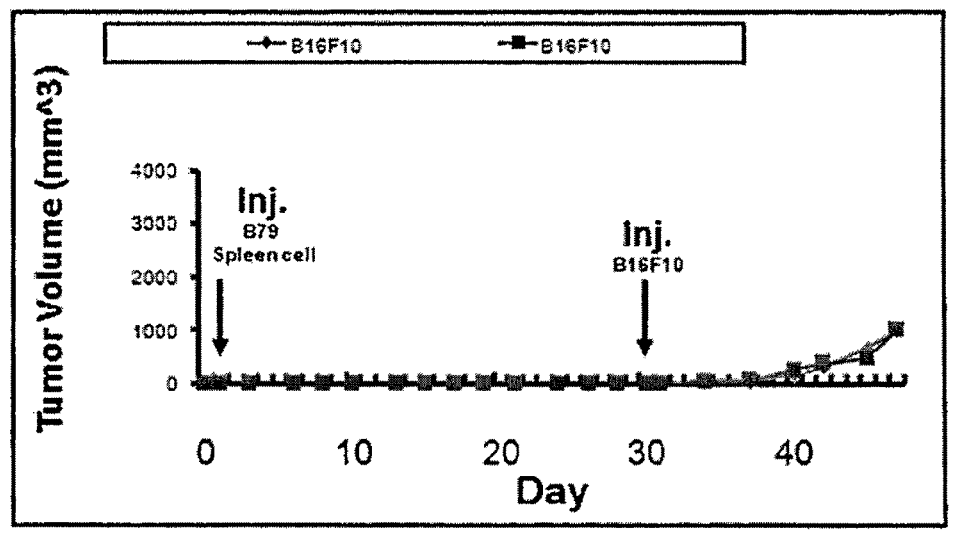
Figure 4C:
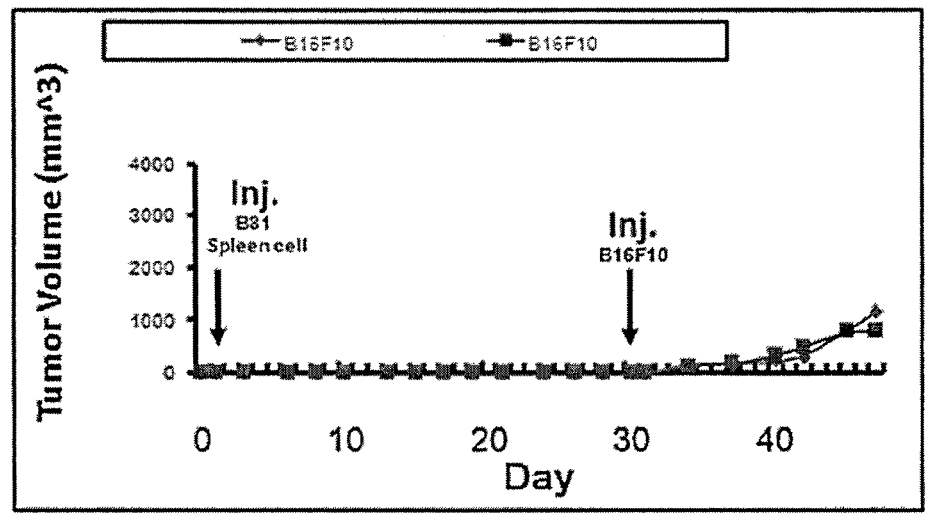
Figure 4C:
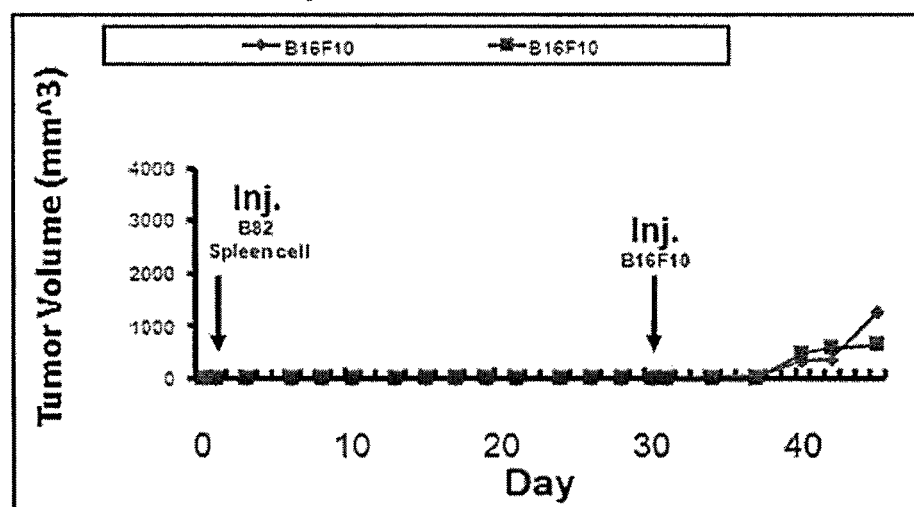
Figure 4C:
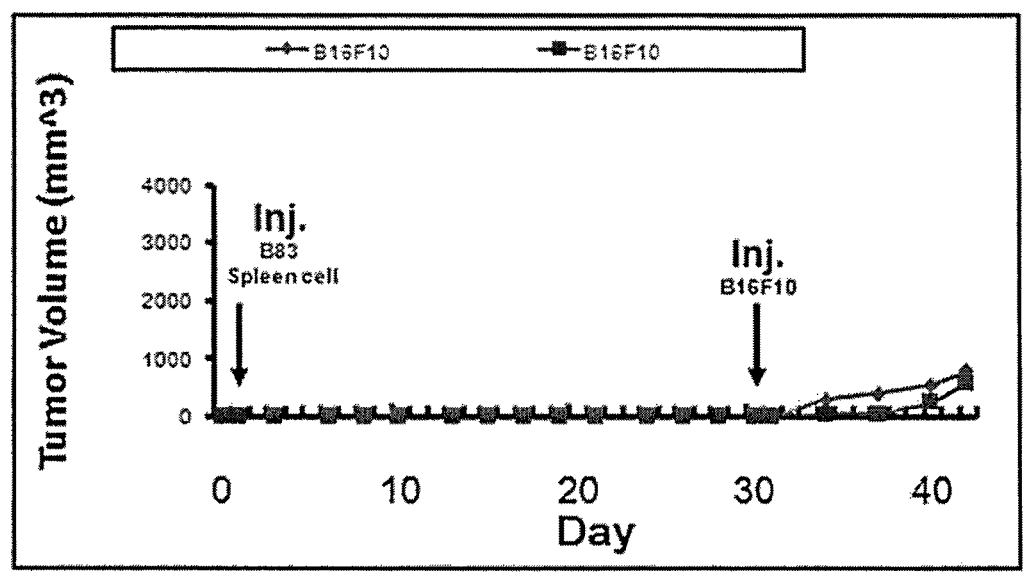

BALB/c mice (B78-B83) were pretreated with Zfra4-10 in the presence or absence of indicated chemicals once per week for three consecutive weeks. A week later post injection, the mice were inoculated with melanoma B16F10 cells. No cancer cell growth was shown in all mice except the PBS control mice (B78). FIG. 4B. Spleen cells from the aforementioned BALB/c mice (B78-B83) were isolated and transferred to immunodeficient NOD-SCID mice (S133-S139) via tail veins. Most of the transferred spleen cells in NOD-SCID mice conferred resistance to the growth of B16F10 cells, except the one from CI-4AS-1 treatment (S136). FIG. 4B Similar experiments were carried out in immunodeficient NOD-SCID mice. FIG. 4C. All the test chemicals alone or in combination were not effective because, unlike BALB/c mice, NOD-SCID mice have no B cells. If B cells are present in mice, CD19 antibodies can effectively boost the effect of Zfra.

Figure 4D:
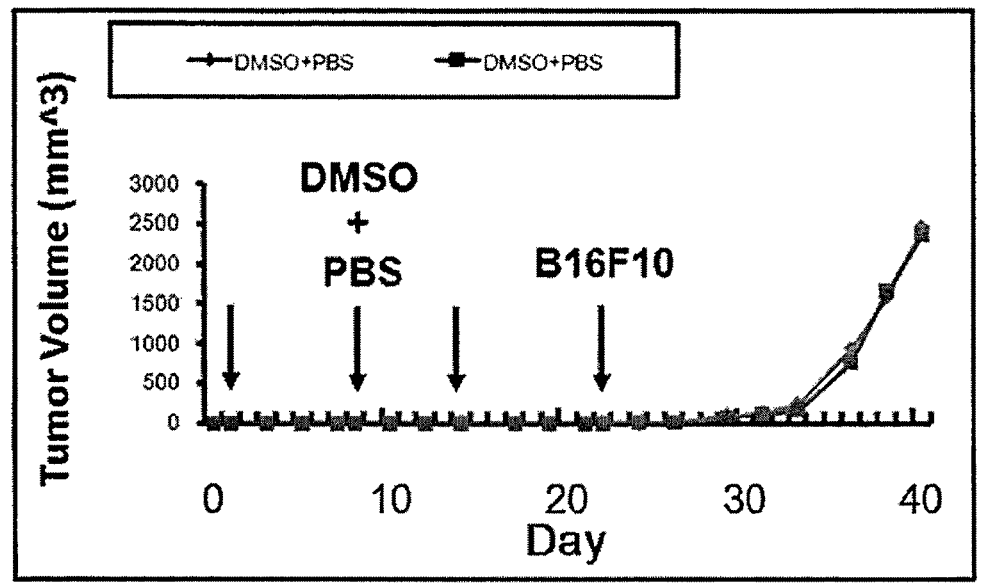
FIG. 4D includes chart showing that most of the transferred spleen cells in NOD-SCID (mice S149-S154) treated as indicated mice conferred resistance to the growth of B16F10 cells, except the one from CI-4AS-1 treatment. Overall, the anticancer efficacy of spleen cells derived from Zfra plus chemical drugs was better than chemical drugs only.
Figure 4D:
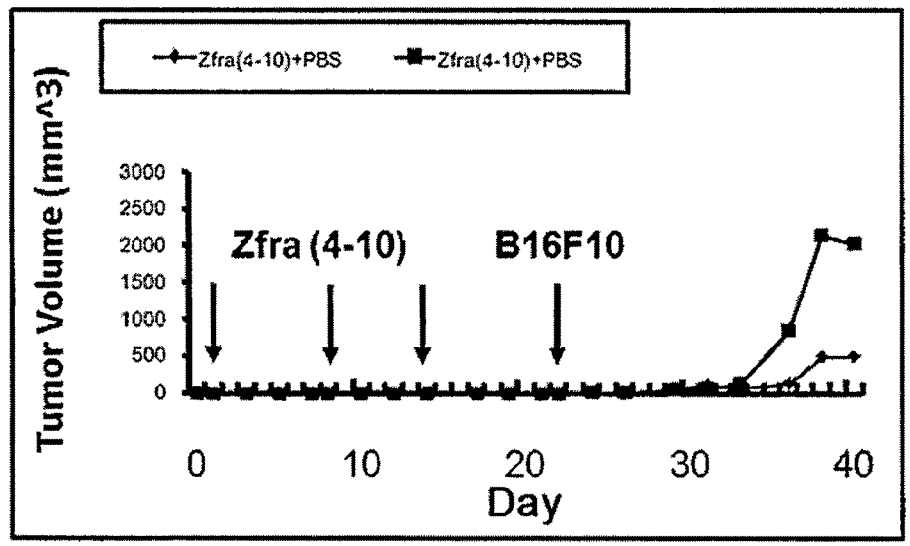
Figure 4D:
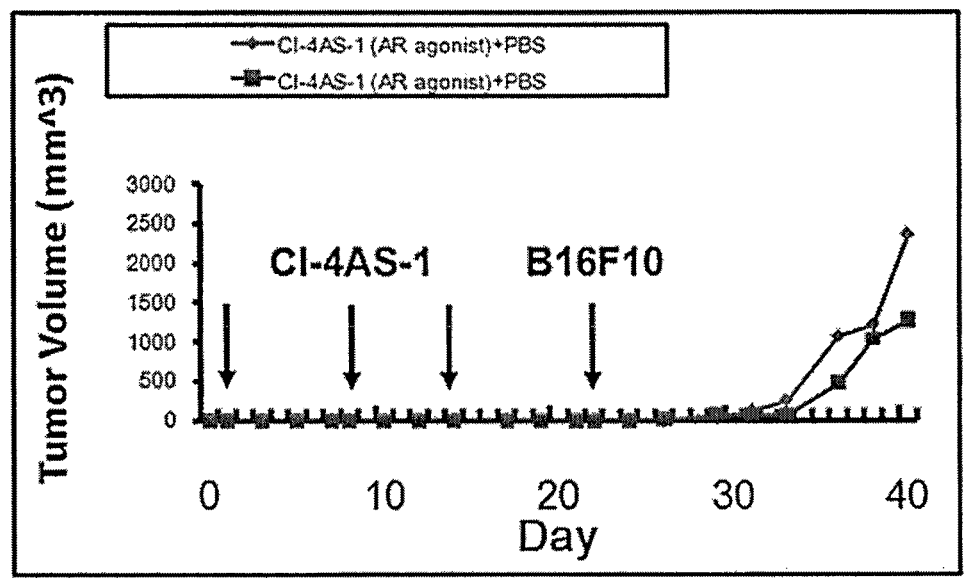
Figure 4D:
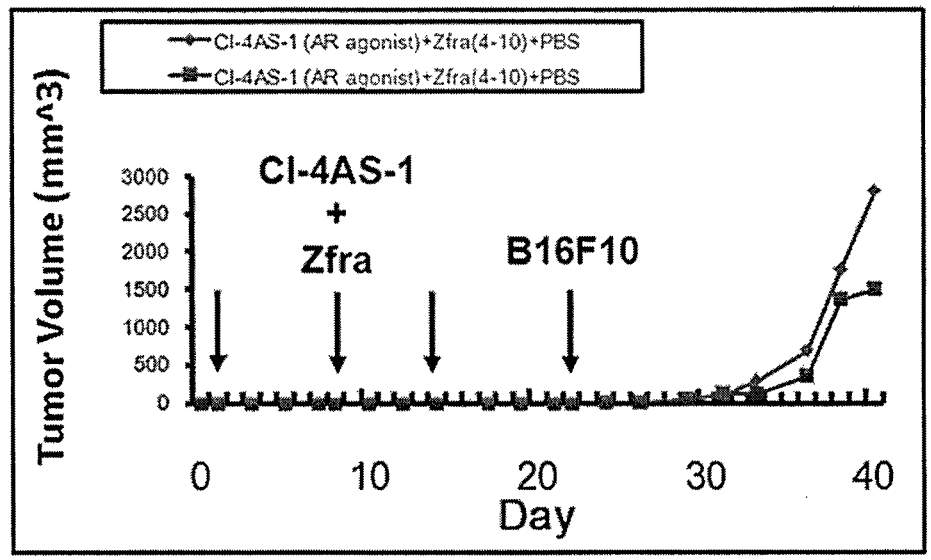
Figure 4D:
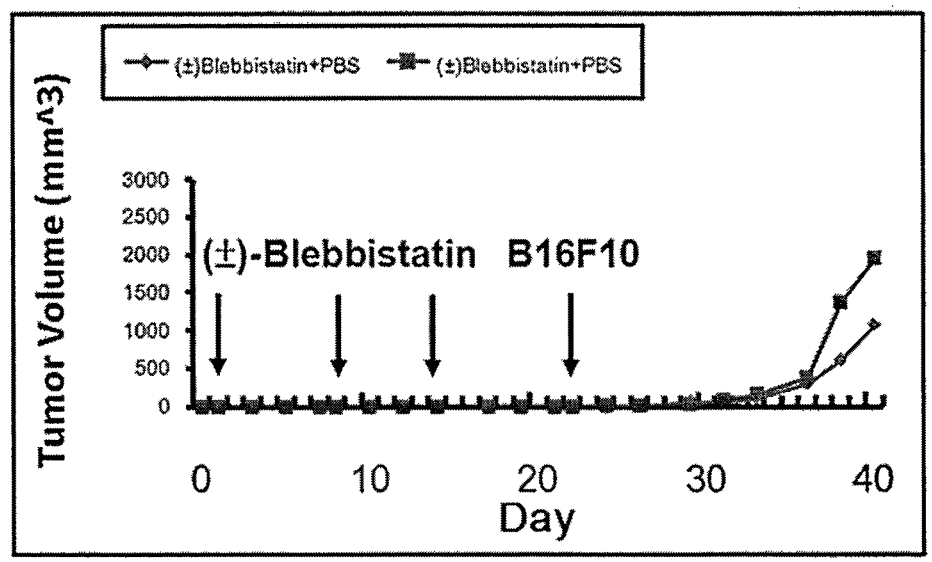
Figure 4D:
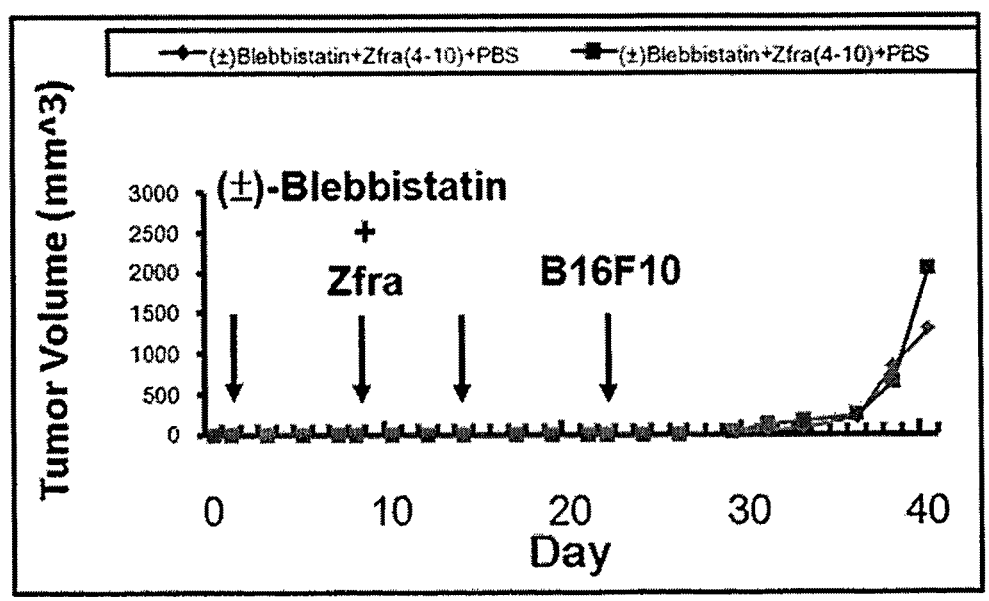

Taken together, the results showed that all of the indicated treatments involving administration of the compounds with or without Zfra peptide blocked the growth of B16F10 cells in BALB/c mice, but only slightly retarded the growth of B16F10 cells in NOD-SCID mice (FIG. 4B and FIG. 4C). In the treatments involving spleen cell transfer, all of NOD-SCID mice displayed resistance to the growth of B16F10 cells, except for the mice treated with only CI-4AS-1 (FIG. 4C and FIG. 4D). Overall, the anticancer efficacy of spleen cells derived from animals receiving Zfra plus chemical drugs was better than chemical drugs alone (FIGS. 4B-4D). More activated Z cells were observed in mice treated with both Zfra peptide and CI-4AS-1 or (±)-Blebbistatin as compared with mice treated with only the Zfra peptide or the compound.

Figure 4E:
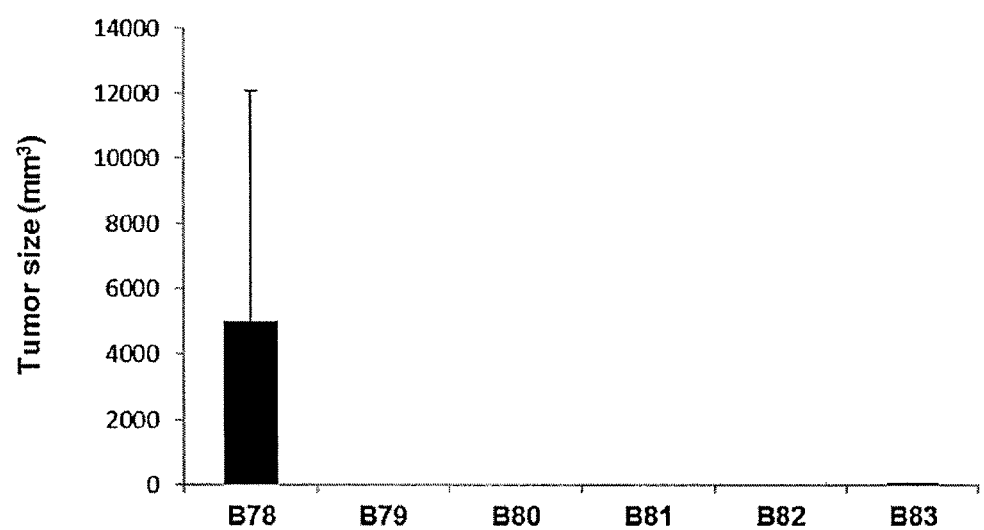
FIG. 4E is a diagram showing the activation of Z cells from spleen cells using Ztra$_{1-31}$ peptide and surface marker analysis of the Z cells thus activated. Spleen cells were isolated and stained with synthesized peptide TMR-Zfra$_{1-31}$ (Tetramethylrhodamine-Zfra, excitation 550 nm, emission 573 nm) for 30 minutes on ice. Surface marker analysis indicated that the anticancer efficacy may essentially work via activating a cluster of memory spleen cells, called "Z cells". N/A=not applicable.
Figure 4E:
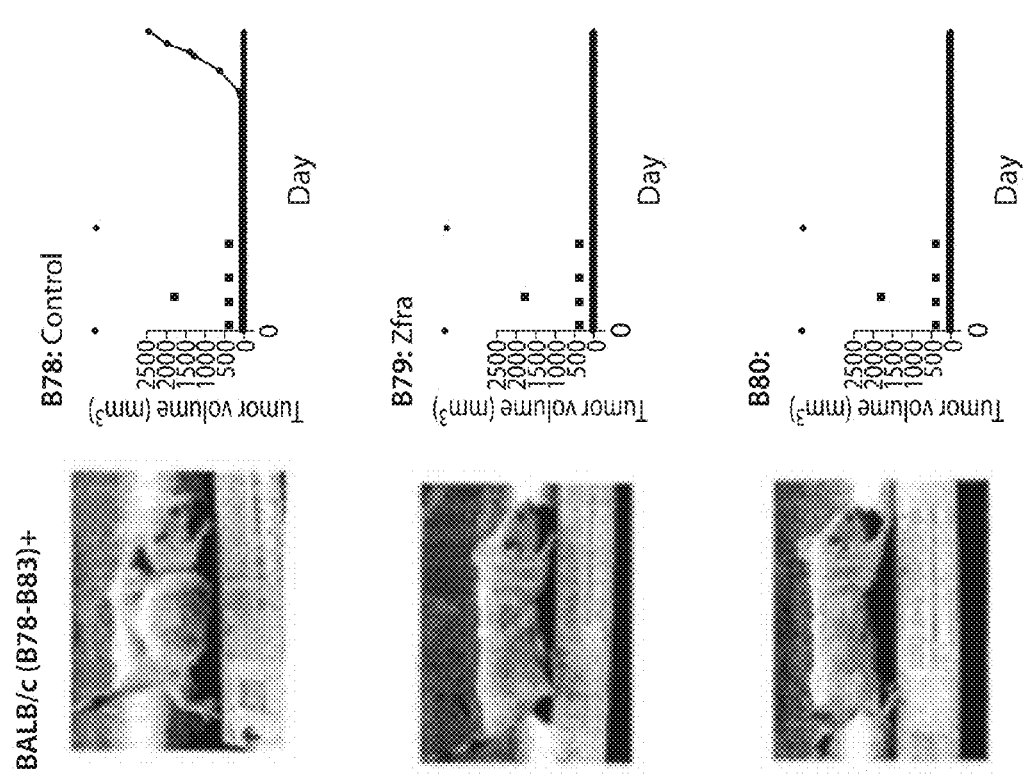
Figure 4E:
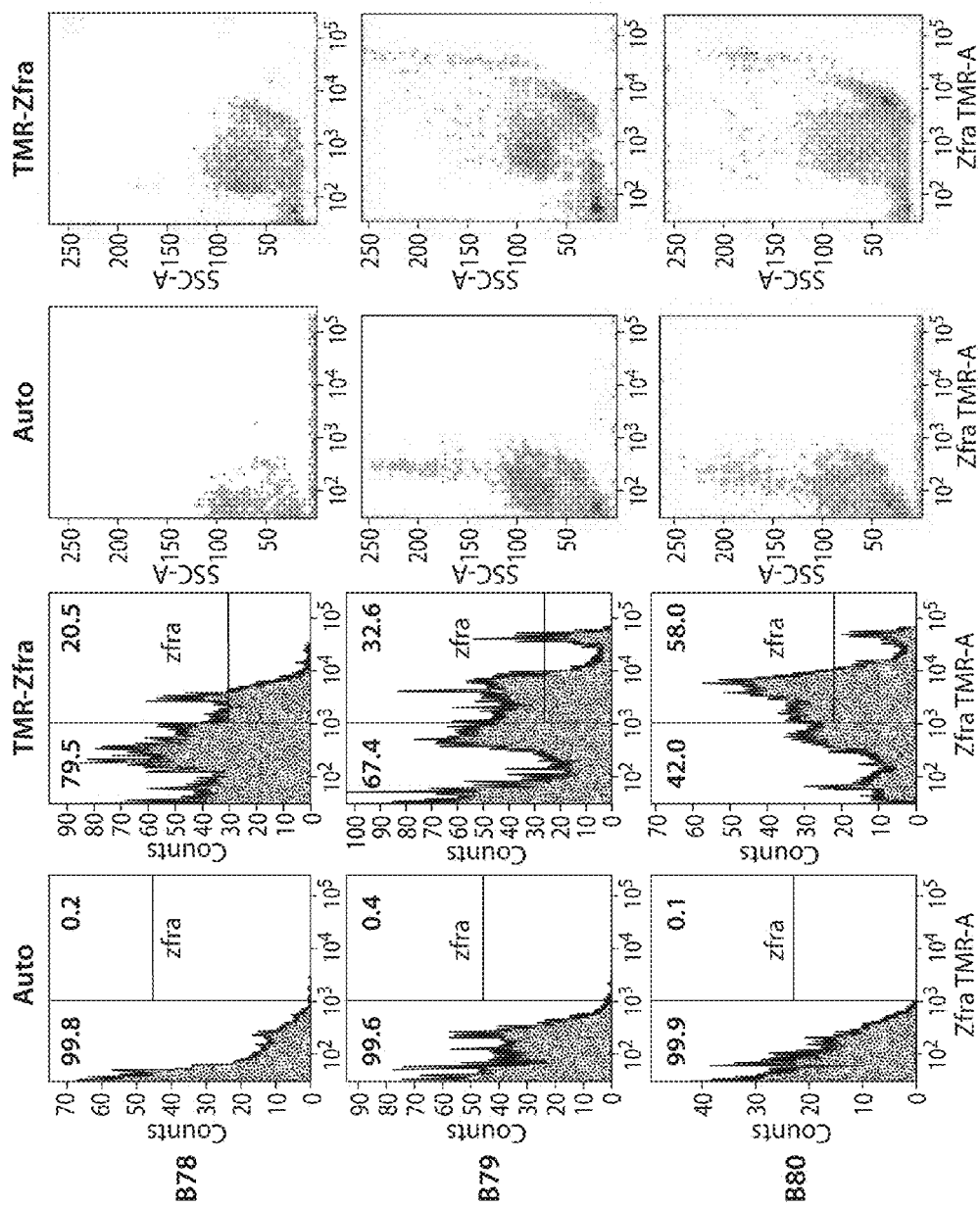
Figure 4E:
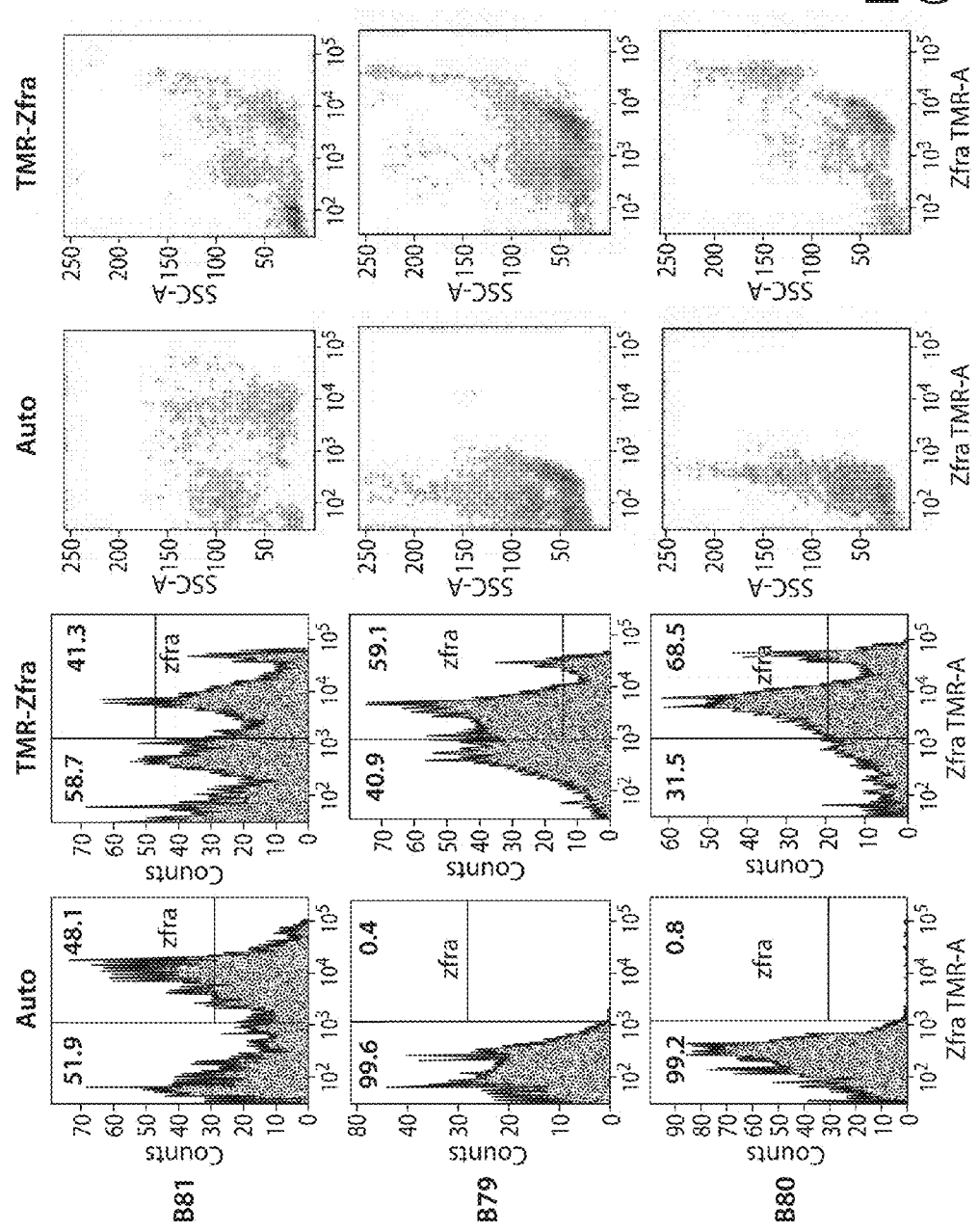
Figure 4E:
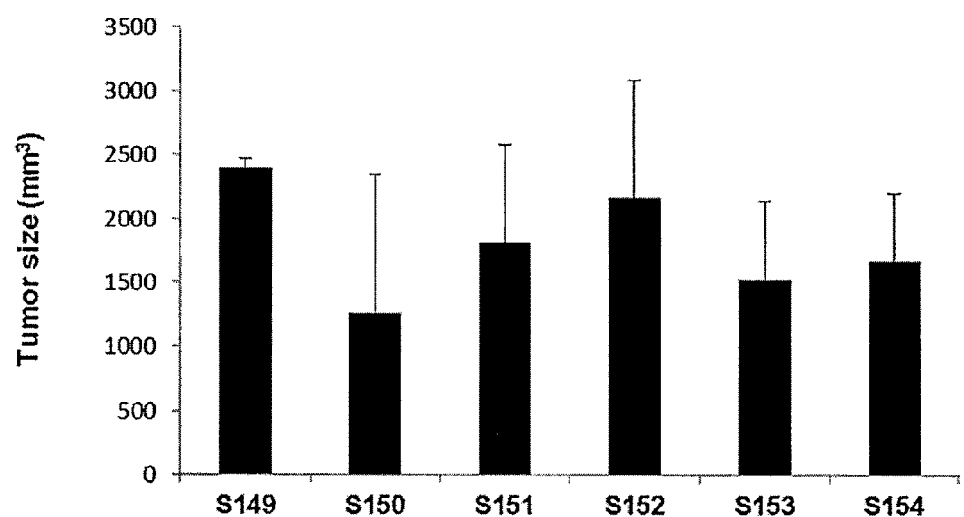

Spleen cells from the mice were isolated and stained with synthesized peptide TMR-$Zfra_{1-31}$ (Tetramethylrhodamine-Zfra, excitation 550 nm, emission 573 nm) for 30 minutes on ice. Surface marker analysis revealed the presence of Z cells, which conferred the anticancer activity (FIG. 4E).

Example 4

In Vitro Activation of Spleen Cells with Zfra Confers Suppression of Cancer Cell Growth As a technical breakthrough, Z cells were successfully activated in vitro to produce a population of immune cells containing Z cells. When transferred into naïve mice, these in vitro prepared Z cells successfully blocked cancer growth.

Figure 5:
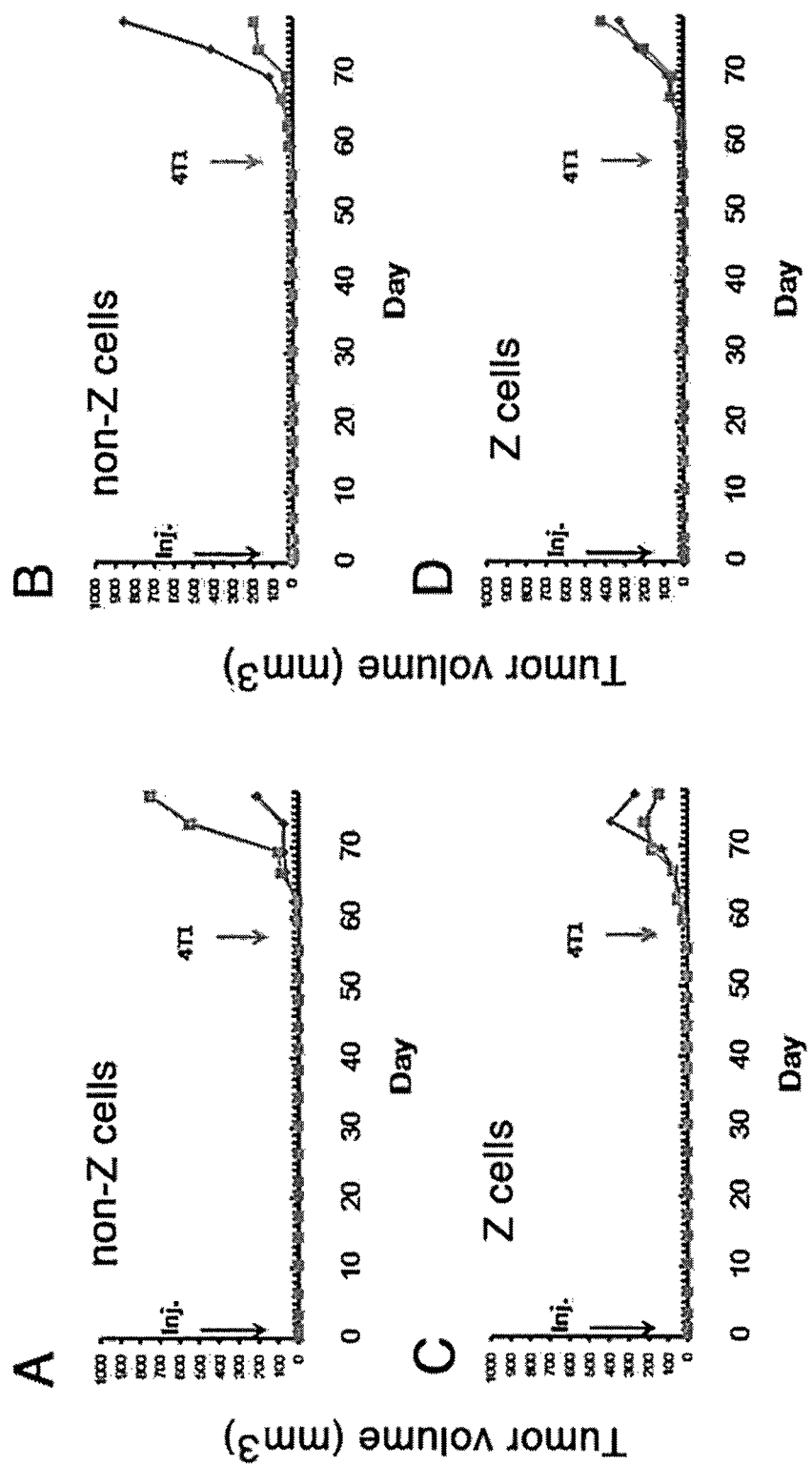
FIG. 5 include charts showing in vitro activation of Z cells for killing breast cancer in vivo. Immune competent BALB/c mice were sacrificed and spleen cells were isolated. These cells were treated with Zfra4-10 for 16-24 hr. Z$^+$ and Z$^-$ cells were isolated by cell sorting. The isolated cells were then transferred to naïve BALB/c mice. Breast cancer 4T1-Luc cells did not grow effectively in mice inoculated with Z$^+$ cells.
Figure 5:
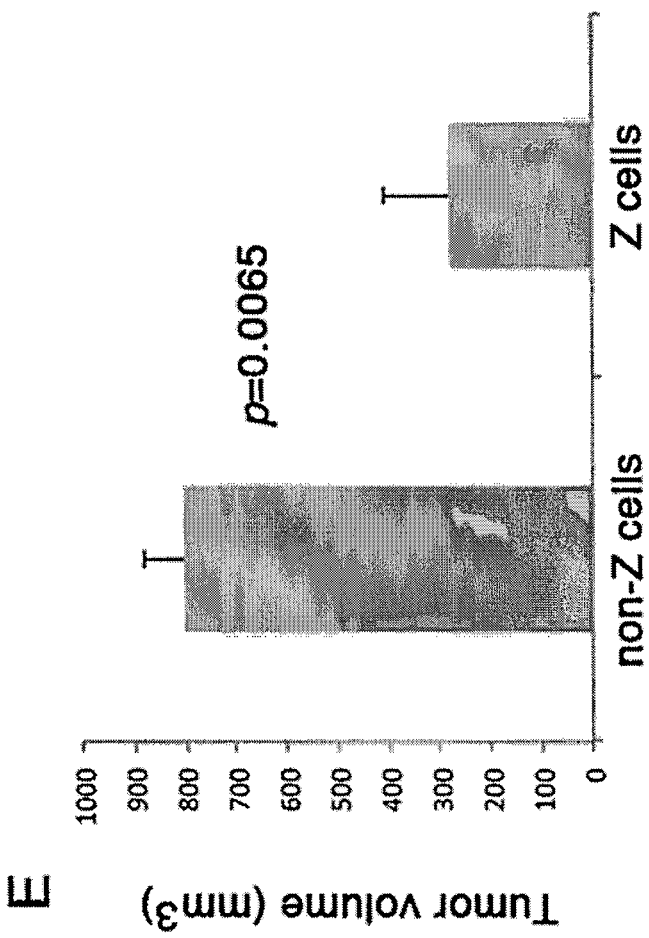

Briefly, spleen cells were isolated from BALB/c mice and then cultured overnight. These cells were stimulated with $Zfra_{4-10}$ peptide (10 μM) for 16-24 hr, and then stained with TMR-Zfra, followed by isolating the cells using a cell sorter. Z+ and Z− cell populations were counted and injected via tail veins of BALB/c. Post injection for 1 week or up to 12 months, these mice were challenged with breast cancer cells and were found that cancer cell growth was significantly suppressed in mice treated with Z+ cell populations as compared with mice treated with Z− cell populations. FIG. 5.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An in vitro cell culture system, comprising (i) an immune cell population, which comprises anti-cancer Z cells, and (ii) CI-4AS-1, Blebbistatin, or a combination thereof.

2. The in vitro cell culture system of claim 1, wherein the immune cell population comprises at least 20% anti-cancer Z cells.

3. The in vitro cell culture system of claim 1, wherein the immune cell population is prepared by a process comprising:

culturing immune cells in vitro in a medium that comprises a peptide comprising the amino acid sequence of RRSSSCK (SEQ ID NO:1) to produce the immune cell population, which comprises anti-cancer Z cells.

4. The in vitro cell culture system of claim 3, wherein the medium further comprises CI-4AS-1 or Blebbistatin.

5. The in vitro cell culture system of claim 3, wherein the immune cells are spleen cells.

* * * * *

SEQUENCE LISTING

<160> NUMBER OF SEQ ID NOS: 3

<210> SEQ ID NO 1
<211> LENGTH: 7

```
<212> TYPE: PRT
<213> ORGANISM: Artificial Sequence
<220> FEATURE:
<223> OTHER INFORMATION: Synthetic Polypeptide

<400> SEQUENCE: 1

Arg Arg Ser Ser Ser Cys Lys
1               5

<210> SEQ ID NO 2
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 2

Met Ser Ser Arg Arg Ser Ser Cys Lys Tyr Cys Glu Gln Asp Phe
1               5                   10                  15

Arg Ala His Thr Gln Lys Asn Ala Ala Thr Pro Phe Leu Ala Asn
            20                  25                  30

<210> SEQ ID NO 3
<211> LENGTH: 473
<212> TYPE: PRT
<213> ORGANISM: Homo sapiens

<400> SEQUENCE: 3

Met Arg Ala Gly Pro Gly Pro Thr Val Thr Leu Ala Leu Val Leu Ala
1               5                   10                  15

Val Ser Trp Ala Met Glu Leu Lys Pro Thr Ala Pro Pro Ile Phe Thr
            20                  25                  30

Gly Arg Pro Phe Val Val Ala Trp Asp Val Pro Thr Gln Asp Cys Gly
        35                  40                  45

Pro Arg Leu Lys Val Pro Leu Asp Leu Asn Ala Phe Asp Val Gln Ala
    50                  55                  60

Ser Pro Asn Glu Gly Phe Val Asn Gln Asn Ile Thr Ile Phe Tyr Arg
65                  70                  75                  80

Asp Arg Leu Gly Leu Tyr Pro Arg Phe Asp Ser Ala Gly Arg Ser Val
                85                  90                  95

His Gly Gly Val Pro Gln Asn Val Ser Leu Trp Ala His Arg Lys Met
            100                 105                 110

Leu Gln Lys Arg Val Glu His Tyr Ile Arg Thr Gln Glu Ser Ala Gly
        115                 120                 125

Leu Ala Val Ile Asp Trp Glu Asp Trp Arg Pro Val Trp Val Arg Asn
    130                 135                 140

Trp Gln Asp Lys Asp Val Tyr Arg Arg Leu Ser Arg Gln Leu Val Ala
145                 150                 155                 160

Ser Arg His Pro Asp Trp Pro Asp Arg Ile Val Lys Gln Ala Gln
                165                 170                 175

Tyr Glu Phe Glu Phe Ala Ala Gln Gln Phe Met Leu Glu Thr Leu Arg
            180                 185                 190

Tyr Val Lys Ala Val Arg Pro Arg His Leu Trp Gly Phe Tyr Leu Phe
        195                 200                 205

Pro Asp Cys Tyr Asn His Asp Tyr Val Gln Asn Trp Glu Ser Tyr Thr
    210                 215                 220

Gly Arg Cys Pro Asp Val Glu Val Ala Arg Asn Asp Gln Leu Ala Trp
225                 230                 235                 240
```

```
Leu Trp Ala Glu Ser Thr Ala Leu Phe Pro Ser Val Tyr Leu Asp Glu
            245                 250                 255

Thr Leu Ala Ser Ser Arg His Gly Arg Asn Phe Val Ser Phe Arg Val
            260                 265                 270

Gln Glu Ala Leu Arg Val Ala Arg Thr His His Ala Asn His Ala Leu
            275                 280                 285

Pro Val Tyr Val Phe Thr Arg Pro Thr Tyr Ser Arg Arg Leu Thr Gly
            290                 295                 300

Leu Ser Glu Met Asp Leu Ile Ser Thr Ile Gly Glu Ser Ala Ala Leu
305                 310                 315                 320

Gly Ala Ala Gly Val Ile Leu Trp Gly Asp Ala Gly Tyr Thr Thr Ser
                325                 330                 335

Thr Glu Thr Cys Gln Tyr Leu Lys Asp Tyr Leu Thr Arg Leu Leu Val
            340                 345                 350

Pro Tyr Val Val Asn Val Ser Trp Ala Thr Gln Tyr Cys Ser Arg Ala
            355                 360                 365

Gln Cys His Gly His Gly Arg Cys Val Arg Arg Asn Pro Ser Ala Ser
            370                 375                 380

Thr Phe Leu His Leu Ser Thr Asn Ser Phe Arg Leu Val Pro Gly His
385                 390                 395                 400

Ala Pro Gly Glu Pro Gln Leu Arg Pro Val Gly Glu Leu Ser Trp Ala
            405                 410                 415

Asp Ile Asp His Leu Gln Thr His Phe Arg Cys Gln Cys Tyr Leu Gly
            420                 425                 430

Trp Ser Gly Glu Gln Cys Gln Trp Asp His Arg Gln Ala Ala Gly Gly
            435                 440                 445

Ala Ser Glu Ala Trp Ala Gly Ser His Leu Thr Ser Leu Leu Ala Leu
450                 455                 460

Ala Ala Leu Ala Phe Thr Trp Thr Leu
465                 470
```